United States Patent
Baksh et al.

(10) Patent No.: US 9,644,182 B2
(45) Date of Patent: May 9, 2017

(54) PROGENITOR CELL POPULATIONS, EXPANSION THEREOF, AND GROWTH OF NON-HEMATOPOIETIC CELL TYPES AND TISSUES THEREFROM

(76) Inventors: Dolores Baksh, Mississauga (CA); John E. Davies, Toronto (CA); Peter Zandstra, Toronto (CA)

(*) Notice: Subject to any disclaimer, the term of this patent is extended or adjusted under 35 U.S.C. 154(b) by 974 days.

(21) Appl. No.: 11/828,575

(22) Filed: Jul. 26, 2007

(65) Prior Publication Data
US 2008/0020459 A1    Jan. 24, 2008

Related U.S. Application Data

(63) Continuation of application No. 10/475,861, filed as application No. PCT/CA02/00550 on Apr. 23, 2002, now abandoned.

(60) Provisional application No. 60/285,701, filed on Apr. 24, 2001, provisional application No. 60/328,110, filed on Oct. 11, 2001.

(51) Int. Cl.
*C12N 5/02*    (2006.01)
*C12N 5/00*    (2006.01)
*C12N 5/0775*   (2010.01)

(52) U.S. Cl.
CPC ...... *C12N 5/0663* (2013.01); *C12N 2501/125* (2013.01); *C12N 2501/23* (2013.01)

(58) Field of Classification Search
None
See application file for complete search history.

(56) References Cited

U.S. PATENT DOCUMENTS 3,850,748 A * 11/1974 Cook et al. .................. 435/392
5,459,069 A * 10/1995 Palsson et al. ........... 435/289.1
5,486,359 A    1/1996 Haynesworth et al.
6,087,113 A    7/2000 Haynesworth et al.

FOREIGN PATENT DOCUMENTS

| WO | 99/49015 | | 9/1999 |
|---|---|---|---|
| WO | 00/27996 A1 | | 5/2000 |
| WO | WO 01/11011 | * | 2/2001 |
| WO | 02/086104 A1 | | 10/2002 |
| WO | 2005/045011 A1 | | 5/2005 |

OTHER PUBLICATIONS

Krebsbach et al., 1999, Crit. Rev. Oral Biol. Med. 10:165-181.*
Kallos et al 1999, Biotechno. Bioeng. 63: 473-483.*
Minguell et al 2001, Expermental Biology and Medicine 226:507-520.*
Baksh, et al. (2003) "Adult human bone marrow-derived mesenchymal progenitor cells are capable of adhesion-independent survival and expansion", Experimental Hematology, 31: 723-32.*
Pittenger et al., "Multilineage Potential of Adult Human Mesenchymal Stem Cells", Science, vol. 284, Apr. 2, 1999, pp. 143-147.
Emerson et al., "Ex Vivo Expansion of Hematopoietic Precursors, Progenitors, and Stem Cells: The Next Generation of Cellular Therapeutics" Blood, vol. 87, No. 8, Apr. 15, 1996, pp. 3082-3088.
Baksh et al., "Soluble factor cross-talk between human bone marrow-derived hematopoietic and mesenchymal cells enhances in vitro CFU-F and CFU-O growth and reveals heterogeneity in the mescenchymal progenitor cell compartment", Blood, vol. 106, No. 9, Nov. 2005, pp. 3012-3019.
Baksh D. et al., "Expansion of Human CFU-O Progenitors in Stirred Suspension Bioreactors" *Journal of Bone and Mineral Research*, 2001, vol. 16, No. Suppl. 1, p. S372, XP-001084727.
Colter D. C. et al., "Rapid Expansion of Recycling Stem Cells in Cultures of Plastic-Adherent Cells From Human Bone Marrow" *Proceedings of the National Academy of Sciences of the United States*, 2000, vol. 97, No. 7, pp. 3213-3218, XP-002205331.
Conget P. A. et al., "Phenotypical and Functional Properties of Human Bone Marrow Mesenchymal Progenitor Cells" *Journal of Cellular Physiology*, 1999, vol. 181, No. 1, pp. 67-73, XP-001085195.
Erices A. et al., "Mesenchymal Progenitor Cells in Human Umbilical Cord Blood" *British Journal of Haematology*, 2000, vol. 109, No. 4, pp. 235-242, XP-002205332.
Kallos M. S. et al., "Extended Serial Passaging of Mammalian Neural Stem Cells in Suspension Bioreactors" *Biotechnology and Bioengineering U.S.*, 1999, vol. 65, No. 5, pp. 589-599, XP-002205334.
Marciniak R. et al., "A Common Precursor Cell for Colony Forming Unit—Fibroblast (CFU-F) and CFU-Osteoblast (0)" *Experimental Hematology (Charlottesville)*, 2001, vol. 29, No. 8, Supplement 1, p. 8, XP-001084719.
Minguell J. J. et al., "Biology and Clinical Utilization of Mesenchymal Progenitor Cells" *Brazilian Journal of Medical and Biological Research*, 2000, vol. 33, No. 8, pp. 881-887, XP-002205335.
Muraglia A. et al., "Clonal Mesenchymal Progenitors from Human Bone Marrow Differentiate in Vitro According to a Hierarchical Model" *Journal of Cell Science*, 2000, vol. 113, No. 7, pp. 1161-1166, XP-002205333.
Zandstra P. W. et al., "Expansion of Hematopoietic Progenitor Cell Populations in Stirred Suspension Bioreactors of Normal Human Bone Marrow Cells" *Biotechnology (Nature Publishing Company) U.S.*, 1994, vol. 12, No. 9, pp. 909-914, XP-001087516.
Deans et al., 2000, *Experimental Hematology* 28:875-884.

* cited by examiner

*Primary Examiner* — Robert M Kelly
(74) *Attorney, Agent, or Firm* — Tarolli, Sundheim, Covell & Tummino LLP

(57) ABSTRACT

Described is a method of expanding human progenitor cells by suspension culturing under non-static conditions. The culturing method provides a three-dimensional space for the rapid expansion of desirable progenitors. By this method, a new compartment of multipotential progenitor cells has been identified, which give rise under differentiation conditions to progeny including osteoblasts, chondrocytes, myoblasts, adipocytes, and other non-hematopoietic cell types. Their use in cell and tissue-based engineering is described.

3 Claims, 21 Drawing Sheets

| Treatment | Osteoblast  | Adipocyte  | Fibroblast  | Neural-like  |
|---|---|---|---|---|
| No Cytokine | + | + | + | - |
| SCF | - | - | + | - |
| IL3 | + | - | + | - |
| MCSF | + | - | - | - |
| PDGF | + | - | - | + |
| SCF+IL3 | + | + | + | - |
| SCF+PDGF | - | - | + | + |
| SCF+IL3+PDGF | + | + | + | + |
| SCF+IL3+FGF | - | - | + | - |

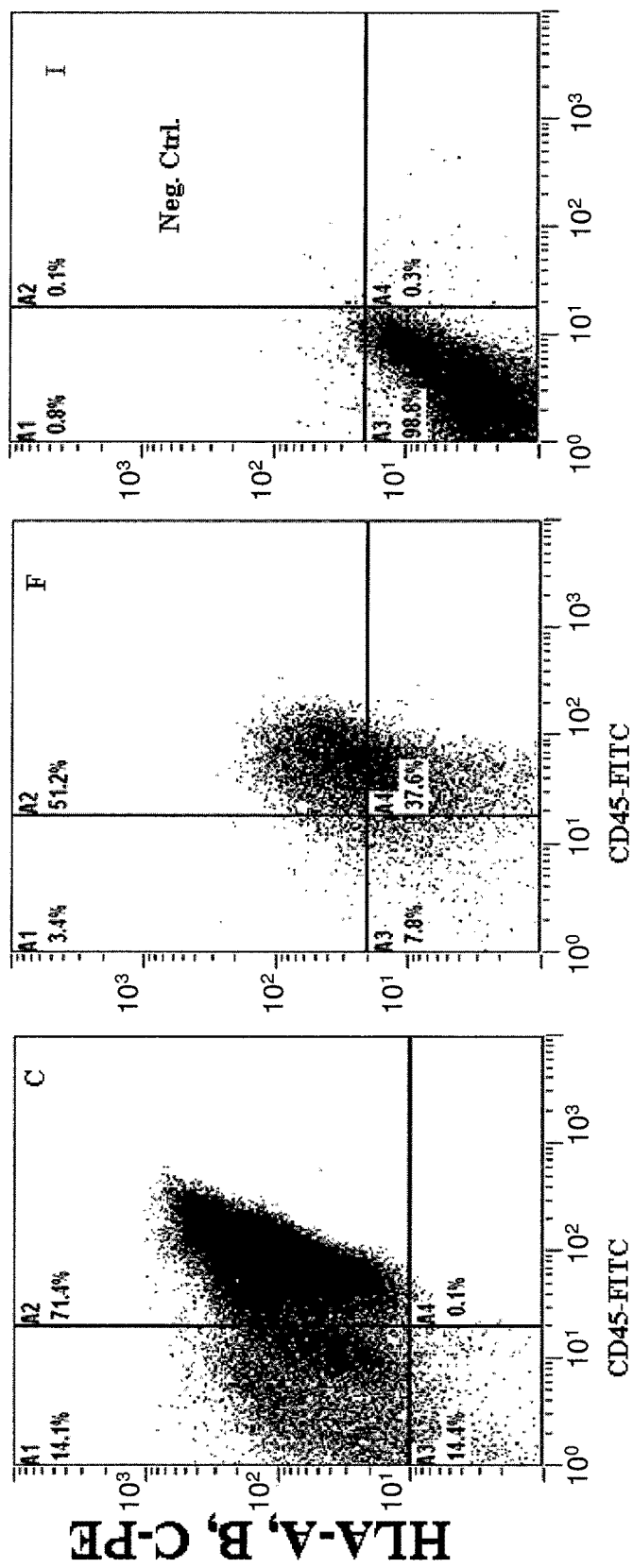

PROGENITOR CELL POPULATIONS, EXPANSION THEREOF, AND GROWTH OF NON-HEMATOPOIETIC CELL TYPES AND TISSUES THEREFROM

CROSS-REFERENCE TO RELATED APPLICATION

This application is a continuation application of 10/475,861 filed on Oct. 24, 2003, abandoned, which is a 371 of PCT/CA02/00550, filed on Apr. 23, 2002, which claims priority from U.S. provisional application 60/285,701 filed Apr. 24, 2001, and from U.S. provisional application 60/328,110 filed Oct. 11, 2001, the entire disclosures of which are incorporated herein by reference.

FIELD OF INVENTION

The present invention relates to the identification and subsequent expansion of a new compartment of progenitor cells which give rise through differentiation to a wide variety of cell types that form tissues including bone, cartilage, fat, muscle, endothelium, adipose and neural cells, among others. The invention further relates to methods by which such cell populations are expanded. Further, the invention relates to methods by which such cell types and tissues are formed, to the cell and tissue types resulting therefrom, and to applications of such progenitor and differentiated cells in cell-based therapy and tissue engineering.

BACKGROUND OF THE INVENTION

One challenge of cell-based therapy and tissue engineering strategies is to bring large numbers of appropriate progenitor cells to the tissue repair and/or regeneration site as expediently as possible. The bone marrow compartment, and particularly the marrow parenchyma, provides an attractive source for such progenitor cells. The marrow parenchyma includes hematopoietic progenitor cells, which differentiate into blood cells of various types. The marrow parenchyma also includes non-hematopoietic progenitor and stem cells, which differentiate into mesenchymal and other cell types, from which various structural and connective human tissues arise. More specifically, the mesenchymal progenitor and stem cells within the marrow parenchyma give rise, through differentiation, to osteogenic cell types that form bone, to chondrogenic cell types that form cartilage, and to myogenic cell types that form muscle and other connective tissues such as bone marrow stroma. Parenchymal progenitors further include cells that give rise to other non-hematopoietic cell types and tissues, which include adipocytes that form adipose tissue, neurons and other neural cells that form nerve tissue, and cells capable of giving rise to endothelium and related vasculature.

The present invention is thus concerned with progenitor and stem cells of the type that are extractable, for instance, from marrow parenchyma, and which give rise to non-hematopoietic cell types. These cells can be referred to as non-hematopoietic progenitors, or NHP cells. As noted, the NHP cells include the mesenchymal progenitor cells (MPCs) and progenitor cells that give rise to other non-blood cell types, and thus as a class, give rise to a wide variety of cell types and tissues of therapeutic interest, including nerve tissue, connective tissue, muscle, tendon/ligament, bone, cartilage, adipose tissue and vascular endothelium.

It is established that the NHPs including the MPCs, can be expanded without differentiating. By this route, the population can be increased from the small numbers first obtained from the bone marrow or other sources, to the large numbers required for their medical use, without concomitantly inducing the cells to differentiate or become committed to development toward a particular cell lineage. To provide these cells in quantity sufficient for medical use, research has accordingly focused on finding novel approaches for ex vivo expansion of progenitor cells, including MPCs. Approaches to-date involve culturing whole bone marrow that contains low frequency of such cells that have been isolated based on their adherence to tissue culture treated substrates [Friedenstein et al., 1992; Castro-Malaspina et al., 1980] and passaging the adherent layer many times to achieve expansion [Colter et al., 2000; Ohgushi et al., 1999; Bruder et al., 1997; Caplan et al., 1997; Jaiswal et al., 1997]. However, the results of this approach have not clearly demonstrated that i) the adherent cell population are true mesenchymal stem cells, ii) that this cell population can be expanded to high numbers suitable for clinical application in an appropriate time frame, while iii) still maintaining the ability of this cell population to form morphologically or histologically identifiable mature mesenchymal cells or tissue, such as bone at each passage.

U.S. Pat. No. 6,087,113 issued Jul. 11, 2000 entitled "Monoclonal antibodies for human mesenchymal stem cells" describes a method for isolating a population of human cells that, based on their expression of specific cell surface antigens detectable using monoclonal antibodies, are enriched in cells capable of giving rise to a variety of mesenchymally-derived tissues. Although this patent claims that mesenchymal stem cells can be identified and isolated by positive binding to such monoclonal antibodies, what is not considered is that these cells have been cultured on an adherent surface and then positively selected, a process that has the potential to change both the phenotype and functional properties of the marrow-derived cell population. This adherence-based approach requires cell-substrate contact not only to isolate so-called mesenchymal progenitor cells but also to achieve their expansion. Other methods of culturing anchorage dependent cells have been described. These include growing cells on the surface of a hollow fibre membrane (Jacques, et al., 1976), encapsulating cells within a semipermeable membrane and then suspending the capsules in growth medium (Jarvis et al., 1985), and culturing cells on a three dimensional matrix like collagen (Naughton et al., 1990) or on microspheres that are then maintained in suspension (Hu et al., 1992).

The approaches aimed at expanding progenitor cells from which mesenchymal and other tissues can differentiate have thus relied on culturing an input cell population on a solid surface, i.e., two dimensionally, to generate a slowly expanding population of cells that are adherent-dependent. A different approach has been applied for the expansion of hematopoietic progenitor cells, as reported by Zandstra et al. (1994). It was shown that hematopoietic cells could be expanded in stirred suspension culture. However, and despite the growing interest in their use in cell-based tissue engineering strategies, there remains a need for a technique by which non-hematopoietic stem and progenitor cells, including the mesenchymal progenitor cells can be expanded more rapidly.

This need arises particularly, although not exclusively, in the bone field. One proposed strategy for using tissue engineering principles to restore bone is to harvest marrow derived cells from the patient, expand a cell population with osteogenic potential in vitro, seed the expanded population onto a three-dimensional carrier and then implant the cell-seeded scaffold into the patient as an alternative to a standard bone graft. While various research groups have achieved aspects of this procedural cascade, the strategy has not yet been successfully employed clinically. Although there may be multiple reasons for this, a major obstacle has been the difficulty associated with generating adequate numbers of cells capable of producing osteogenic cells from marrow harvests.

It would therefore be very advantageous to provide an economical method for proliferating large numbers of non-hematopoietic progenitor cells to provide an expanded cell population which can then be used for growing different functional tissues as required.

It would also be useful to provide a cell population that is capable of differentiating into a wide variety of desired tissues.

It would also be desirable to provide such cells in forms that are useful medically for the regeneration and repair of human tissues.

SUMMARY OF THE INVENTION

It has now been found that non-hematopoietic progenitor cells, particularly but not exclusively mesenchymal progenitor cells, can usefully be expanded in non-static suspension culture. More particularly, it has been found that non-hematopoietic progenitor cells of the type recoverable from bone marrow and comparable sources can be expanded significantly in stirred suspension bioreactors. Moreover, the progenitor cells expanded in non-static suspension culture retain the potential to differentiate into a variety of cell types other than blood cells, including neuronal and endothelial vascular tissue as well as the mesenchymal tissues including bone, cartilage, connective tissue, muscle, tendon and adipose tissue.

By adopting the non-static approach to suspension culturing for expansion of progenitor cells, the present method enables progenitor cell expansion at a rate and efficiency that far surpasses known expansion techniques that rely on and are limited by two dimensional surfaces such as tissue culture plates and tissue flask surfaces. Moreover, the present method of culturing the extracted progenitor cells in suspension avoids the known techniques in which progenitor cells destined for expansion are first selected and then maintained in an adherence-dependent environment that influences and limits the phenotype of cells that can be expanded by those known techniques.

It is believed, more particularly, that the technique of non-static suspension culturing, without prior selection of input cells based on anchorage or adherence, reveals for the first time a new compartment of hitherto unrecognized, multipotential progenitor cells from which an extensive variety of differentiated cell progeny can arise.

According to one aspect of the present invention, there is provided a method in which an input cell population comprising non-hematopoietic progenitor cells is first obtained, and the input cell population is expanded by the step of maintaining that input population in non-static suspension culture for a period sufficient to expand cells with properties of the input population.

The input cell population can comprise non-hematopoietic progenitor (NHP) cells of various classes or types, and particularly includes mesenchymal progenitor cells (MPCs). Thus, in a particular aspect, the present invention provides a method of expanding an input cell population comprising NHP cells, comprising the steps of:
1) providing a cell suspension comprising said cells and a suitable growth medium; and
2) maintaining said cell suspension under non-static culturing conditions for an effective period of time to proliferate cells within the input population.

In another, more particular aspect of the present invention, there is provided a method of expanding an input cell population comprising mesenchymal progenitor cells, comprising the steps of:
1) providing a cell suspension comprising mesenchymal progenitor cells and a suitable growth medium; and
2) maintaining said cell suspension under non-static culturing conditions for an effective period of time to proliferate said cells.

In accordance with this method of the present invention, the input cell population is not subjected to prior selection for adherent or anchorage-dependent cells.

In another of its aspects, the present invention provides an input cell population which is amenable to expansion by non-static suspension culturing thereof, wherein the input cell population comprises a cell population that is enriched for non-hematopoietic progenitor cells. Desirably, the input population is enriched for marrow parenchymal cell progenitors, and especially for mesenchymal progenitor cells. In embodiments of this aspect of the present invention, such enriched input populations are characterized by the substantial absence of at least one hematopoietic cell type, i.e., a cell type bearing a surface marker specific to hematopoietic cells. In particular embodiments, the input population is prepared by enriching a progenitor cell population for mesenchymal progenitor cells. In another embodiment, the input population is prepared by enriching for non-hematopoietic marrow parenchymal progenitors other than mesenchymal progenitors.

The input cell population can be extracted from bone marrow, particularly human bone marrow that is either cadaveric or, more desirably from a fresh source, or from any comparable source such as embryos, umbilical cord blood and the like, in accordance with extraction techniques established for progenitor stem cells. To prepare the input population, the extract is suitably subjected to fractionation using, for instance, commercially available density gradient media that such as Ficoll-Paque™ (Sigma).

In the alternative and in order to prepare an enriched input population for expansion by suspension culturing, the extracted progenitor cells can be subjected to a selection procedure that allows for subtraction (or depletion), from the extract, of cells having a phenotype that is not desired, such as a hematopoietic progenitor cell phenotype. Such enrichment can be achieved, for instance, using the fluorescence-activated cell sorting device and technique, or by application of the established resetting technique. Both techniques utilize antibodies directed at a surface marker unique to a cell type of interest. In essence, both techniques utilize the binding interaction between the antibody/marker to allow cells of that phenotype to be extracted from the cell population undergoing expansion.

These techniques, and related techniques that similarly allow for cell selection, are useful to provide a variety of input cell populations suitable for expansion by non-static suspension culturing, in accordance with the present invention. In particular embodiments, the input population comprises an enriched input population of progenitors that is substantially devoid of at least one hematopoietic cell type, which cell type is characterized by the presence of at least one surface marker selected from CD3, CD14, CD38, CD66 and CD119. In another embodiment of the invention, the input cell population is enriched for cells that lack one or more surface markers associated with the major histocompatibility complex type I (MHC-I) and/or lack one or more surface markers associated with the major histocompatibility complex type II (MHC-II). In particular, the input cell population is desirably enriched for cells that lack one or more, and desirably all, of the following surface markers: HLA-A, HLA-B, HLA-C, HLA-DR, HLA-DP and HLA-DQ.

Thus, in one of its aspects, the present invention provides a novel input cell population for suspension culturing to provide an expanded cell population from which non-hematopoietic and particularly mesenchymal cell types and tissues can be grown, the input cell population comprising a progenitor cell population that has not been adherence-selected and which is enriched for non-hematopoietic progenitor cells. In embodiments, such enriched input progenitor cell population is characterized by the substantial absence of cells expressing one or more hematopoietic progenitor cell surface markers. In particular embodiments, the novel input cell population is characterized by the substantial absence of cells bearing at least one surface marker selected from CD3, CD14, CD38, CD66, and CD119. In other embodiments, the novel input cell population is characterized by the substantial absence of cells bearing at least one marker of MHC, selected from HLA-A, HLA-B, HLA-C, HLA-DR, HLA-DP and HLA-DQ. In a specific embodiment, the novel input cell population is characterized by the substantial absence of all MHC marker-bearing cells.

The input cell population, or the enriched input cell population, is expanded by the technique of non-static suspension culturing. The input cell population is considered "expanded" when the input population has proliferated, and the numbers of cells with one or more of the functional and phenotypic properties of the input population has increased, relative to the number of input cells seeded in suspension culture. Suspension culturing under non-static conditions is performed in a bioreactor or other suitable environment that allows for the 3-dimensional culturing of cells in liquid medium under conditions of temperature, pressure and nutrition amenable to their expansion. Non-static suspension culturing further involves agitation of the culturing environment, as a means to maintain the cultured cells in suspension as individual cells during their expansion. Such agitation typically entails mechanical agitation such as stirring, but may also utilize other fluidizing techniques such as percolation, aspiration, and the like. To minimize adherence during culturing, the bioreactor suitably is treated, e.g., siliconized, to inhibit cell adherence to the internal surfaces of the bioreactor.

In embodiments, the suitable medium may be a hematopoietic culture environment and the suspension may be in a stirred bioreactor. In other embodiments, the medium may be adapted to exclude nutrients of a type typically required for the culturing of hematopoietic progenitor cells and which are necessary only for the maintenance of such hematopoietic cells. For instance, typically the nutrient liquid medium does not require hydrocortisone, and similar supplements that have been utilized predominantly for hematopoietic cell maintenance.

Desirably, expansion of the functional capacity of the input cell population is performed in a medium supplemented with cytokines and/or growth factors, or cellular sources thereof, useful to maintain cell viability over the culturing period. Particularly useful supplements include IL-3 and stem cell factor (SCF, known also as steel factor (SF)). Also particularly useful are such growth factors as platelet-derived growth factor (PDGF), and fibroblast growth factor (FGF), which are valuable in expanding input cell populations capable of giving rise to neuronal cell types. Still other growth factors and cytokines and other supplements can be utilized in accordance with culturing practices established for cell types of particular interest.

Expansion of the functional capacity of the input cell population can be achieved after non-static suspension culture for a matter of days, and culturing periods in the 1-3 week range and longer are also suitable.

As noted, the progenitor cells maintained in suspension are multipotential and include mesenchymal and other progenitor cells. Accordingly, the expanded population may be used to form differentiated phenotypes including bone, chondrocytes, adipocytes, endothelial cells, neural cells, myoblast cells and cartilage. In accordance with aspects of the present invention, once the input population of progenitor cells has been proliferated, i.e., expanded, some or all of the cells can be placed in the appropriate differentiation environment to grow the desired tissue.

The present invention further provides an isolated population of expanded human progenitor cells, characterized in that:
1) when subsequently cultured under conditions appropriate for differentiation, said population gives rise to differentiated cell types that include bone cells, muscle and neuronal cells;
2) the population has been expanded in non-static suspension culture;
3) the progenitor cells within the population have not been selected on the basis of adherence;
4) the population phenotype is SH4 negative; and
5) the population results from culturing in the absence of at least one hematopoietic stem cell-specific culturing supplement.

In another of its aspects, the present invention provides an expanded population of human mesenchymal progenitor cells which result from the non-static suspension culturing of an input population enriched for non-hematopoietic progenitor cells, as described above.

In another of its aspects, the present invention provides a therapeutic composition, useful for delivering human mesenchymal progenitor cells to an environment conducive to the formation of differentiated cells therefrom, the composition comprising a population or subpopulation of human progenitor cells as described above, and a physiologically acceptable vehicle for delivering said cells to said environment.

In embodiments of the present invention, the vehicle is one suitable for delivering the cells to a bone site at which repair or regeneration is desired. In a particular embodiment, the vehicle used to deliver the cells is a matrix material that is compatible with bone and may itself comprise osteoinductive material.

In another of its aspects, the present invention provides an expanded progenitor cell population as described above in combination with factors suitable for inducing the differentiation thereof. Such a combination is manifest as an assay environment, as a tissue growth environment of the type used to prepare tissue for implantation or of the type established following treatment of a human or other patient to provide for tissue repair or regeneration.

In still another of its aspects, the present invention provides a method for producing differentiated, non-hematopoietic cell types, comprising the steps of obtaining an expanded progenitor cell population of the type described above, or a subpopulation thereof, and then delivering that population of cells either per se or in a suitable delivery vehicle to an environment which supports differentiation thereof into a desired cell type. In embodiments of the present invention, the cells are delivered to an environment suitable for inducing their differentiation into a parenchymal cell or tissue selected from bone, cartilage, muscle, adipose, tendon, cartilage, and neurons. In a specific embodiment, the mesenchymal progenitor cells are exploited for the purpose of repairing or regenerating bone, and are therefore delivered to a bone site at which such endpoints are desired.

BRIEF DESCRIPTION OF THE DRAWINGS

Embodiments of the invention will now be described, by way of example only, with reference being had to the drawings, in which:

FIG. 6 provides flow cytometric dot plots of various cell populations at different time points throughout suspension culturing.

FIG. 10A shows a graphical representation of the growth of RosetteSep™-derived human bone marrow-derived cells cultured in stirred suspension bioreactors in the absence and presence of SCF+IL3. FIG. 10B shows a tetracycline incubated bone nodule assays (5 weeks) initiated with cells derived from the SCF+IL3 bioreactor treatment group at Day 7, while FIG. 10C is a dark field micrograph (50×) showing a mineralized nodular area.

DETAILED DESCRIPTION OF THE INVENTION

Figure 1A:
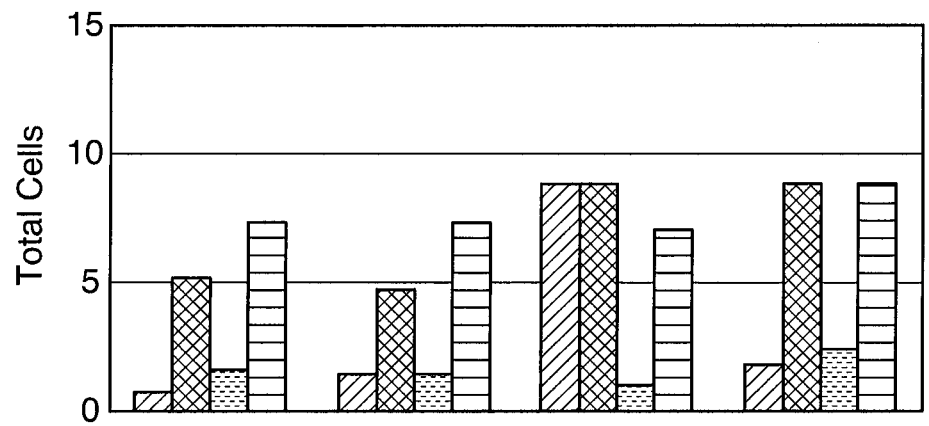
FIG. 1A is a graphical representation illustrating the change in total cell number with time relative to input numbers from density gradient separated human bone marrow-derived cells maintained in a stirred suspension bioreactor (see also FIG. 8)

The invention relates to human progenitor cells from which a variety of non-hematopoietic cell types can differentiate. Because of the variety of non-hematopoietic cells that can differentiate from the present progenitor cell population, it is referred to herein as a population of non-hematopoietic progenitor (NHP) cells. Such a population comprises mesenchymal progenitor cells (MPCs), as well as other non-hematopoietic progenitor cells. Such progenitor cells may also be referred to as "precursor" cells, and these terms are considered equivalent herein for the reason that both progenitors and precursors are able to give rise to differentiated cell type.

The present progenitor cell population results from the non-static suspension culturing of cells of the type obtained from bone marrow, using techniques that are described in greater detail in the examples herein. It is to be appreciated that other comparable and known sources of such progenitor cells can also be used, as noted hereinabove, including particularly umbilical cord and placental blood, peripheral blood, skin, adipose, and muscle.

In order to expand progenitor cells within a cell population, the present invention applies a non-static approach to culturing. This is distinct from established methods that are static, and which are designed not to disturb cells undergoing expansion. Rather, in the present method, the cells are cultured under non-static conditions that introduce agitation and thereby produce cultures in which the cells a present as non-adherent individual cells, and not as either large clumps or as confluent layers. The agitation source is typically a mechanical agitation means that either introduces movement either directly within the culturing medium or externally through the surface on which the culturing vessel is placed. In embodiments, the non-static conditions are introduced by stirring means, which can include a magnetized stirring paddle that is placed the bioreactor and is induced by external magnetizing means. Alternatively, the agitation can be introduced by other means that include fluidized culturing beds, which introduce agitation through the movement of appropriate culturing atmosphere through the cell population.

It will be appreciated that the magnitude of the agitation will be that which is sufficient to maintain the cells in suspension substantially as individual, expandable cells with desired circulation of culturing nutrients, but insufficient to introduce shear forces that will result in cell lysis. The optimum stirring speed is about 40 rpm under the experimental conditions noted herein.

In one embodiment, the culture system was configured such that i) the impeller was placed in the middle of the bioreactor at a 90° angle to the solution surface to maintain axial flow, ii) a constant mixing speed of 40 rpm was used to maintain the cells in suspension and iii) the agitator was positioned three quarters of the way down the vessel to ensure uniform mixing.

With the non-static approach, the present method introduces a three-dimensional environment for cell expansion, and raises exponentially the volume of the environment within which progenitor cells can be expanded, thereby offering increases not only in the number of cells that can be expanded at any given time but also accelerating the rate at which the cells can be expanded over time. In the present method, suitable culturing volumes can range from the milliliters to many liters, for instance from about 0.1 L to more than 200 L, e.g., 0.5 L to 100 L, such as 1 L to 10 L.

Suitable culturing media for use in the present method, as well as culturing temperature and atmosphere are those well established in the art for the culturing of progenitor cells. Temperatures suitably lie within the physiological range. The culturing atmosphere is desirably the appropriate blend of $O_2$ and $CO_2$, e.g., humidified 5% $CO_2$ in air. Culturing medium is any appropriate liquid medium particularly including the commercially available long term culturing (LTC) media, which desirably is supplemented with agents useful in the expansion of non-hematopoietic progenitor cells, such as various growth factors and nutrient supplements. In preliminary studies exemplified herein, each culture received a different cytokine treatment that included the following combinations: no cytokines, SCF, IL3, MCSF, SCF+IL3, SCF+PDGF and SCF+IL3+PDGF. The selection of these growth factors was based on previous reports of their effects on the growth of fibroblasts and other associated mesenchymally-derived cells (see for instance Wang, et al, *Exp. Hematol.* 18, 341-347 (1990); Hirata et al, *Acta Haematol.* 74, 189-194 (1985), and Yamada et al, *J. Cell Physiol* 184, 351-355 (2000).

Suitable culturing periods will be determined largely based on the number of progenitor cells demanded from the expansion process. Under conditions noted in the examples, the numbers of progenitor cells can readily be expanded 5-10 fold over a one week period from initial seeding, with longer term culturing providing further increases in progenitor cell numbers.

The present progenitor cell population results from non-static suspension culture of the bone marrow derived input cell population, or an enriched subpopulation thereof, and is produced without an intervening step of selection based on cell adherence or anchorage dependence, which is more common in the art, and which in itself is believe to impart certain phenotypic traits to the prior art cell populations that are not reflected in the present cell population. The present population is also distinct from a homogeneous mesenchymal stem or progenitor cell population in its ability to give rise to differentiated cell progeny including endothelial cells, and cells forming neuronal tissue, including those displaying neurite outgrowth. Moreover, the present progenitor cell population can be sustained in culture media that lacks one or more artificial media supplements used commonly in the culturing of hematopoietic stem cells, such as hydrocortisone.

In addition to the input cell population just described, the present invention also provides a progenitor cell population that is enriched for non-hematopoietic cells, relative to the extracted population. Such enriched input cell populations include cell populations from which one or more hematopoietic cell types have been subtracted, and those input cell populations to which one or more non-hematopoietic progenitor cells have been added. In embodiments of the invention, the enriched human mesenchymal progenitor cells are represented by cell populations from which one or more cells of a hematopoietic phenotype are subtracted. Specific examples of cell phenotypes that can be subtracted to arrive at the present enriched populations include cells types bearing one or more of the following markers: CD3, CD14, CD38, CD19, CD66, CD119, and cells bearing markers of the major histocompatibility complex types I and II, which include HLA-A, HLA-B and HLA-C (for MHC-I) and HLA-D, HLA-E and HLA-F (for MHC-II).

The generation of such enriched progenitor cell populations can be achieved using the FACS procedure in combination with antibodies to markers on the cell types to be subtracted. Such antibodies, and procedures and devices for performing such subtractions are commercially available.

The procedure can be applied either to the cells following their extraction and prior to suspension culturing, or the procedure can also be applied to the expanded population before being subjected to a differentiation environment, e.g., prior to its formulation or subsequent use for tissue production.

The cell populations generated from the input progenitor cell populations are useful medically in various therapies designed to repair or regenerate tissue of any type into which these populations can differentiate. Thus, for medical use, the expanded mesenchymal progenitor cell population can be formulated for delivery to the site at which differentiation is desired, using any delivery vehicle that is physiologically tolerable to both the recipient and to the viability of the cells formulated therein. Particular formulations and suitable delivery vehicles are known in the art, and will be apparent from the nature of the intended therapy. Desirably, the formulation further contains agents, such as growth factors and cytokines, that enhance the viability and/or the differentiation of the administered cells.

The present invention also provides a method of using specifically differentiated cells for therapy comprising administering the specifically differentiated cells to a patient in need thereof. It further provides for the use of genetically engineered multipotent stem cells to selectively express an endogenous gene or a transgene, and for the use of the progenitor cells either per se or in expanded form in vivo for transplantation/administration into an animal to treat a disease. The cells can be used to engraft a cell into a mammal comprising administering autologous, allogenic or xenogenic cells, to restore or correct tissue specific structural or other function to the mammal. The cells can be used to engraft a cell into a mammal, causing the differentiation in vivo of cell types, and for administering the progenitor or differentiated cells into the mammal. The cells, or their in vitro or in vivo differentiated progeny, can be used to correct a genetic disease, degenerative disease, neural, or cancer disease process. They can be used to produce gingiva-like material for treatment of periodontal disease. They could be used to enhance muscle such as in the heart. A genetically engineered progenitor cell, or its differentiated progeny, can be used to treat a disease with CNS deficits or damage. Further the progenitor cells, or neuronally related differentiated progeny, can be used to treat a disease with neural deficits or degeneration including among but not limited to stroke, Alzhemier's, Parkinson's disease, Huntington's disease, AIDS associated dementia, spinal cord injury, metabolic diseases effecting the brain or other nerves.

The progenitor cells, or cartilage differentiated progeny, can be used to treat a disease of the joints or cartilage such as cartilage tears, cartilage thinning, and osteoarthritis. Moreover, the cells or their osteoblast differentiated progeny can be used to treat bone disorders and conditions, such as bone fractures, osteoarthritis, bone voids caused by surgery or tumors for tissue regeneration in osteoporosis, Paget's disease, and osteomyelitis.

As noted, inducing the progenitor cells, and their expanded equivalents, to differentiate is achieved using techniques established in the art, which vary according to the differentiated cell type desired. For differentiation to osteoblasts, progenitors can be cultured for about 14-21 days in culturing medium comprising supplements such as dexamethasone, β-glycerophosphate and ascorbic acid, and optionally including various bone growth factors. The presence of osteoblasts can be confirmed by Von Kossa staining, or antibodies against a bone cell marker such as bone sialoprotein, osteonectin, osteopontin and osteocalcin.

For differentiation into chondroblasts, the progenitors can be grown in serum-free DMEM supplemented with TGF-β in suspension culture, for about 14 days or more.

To induce adipocyte differentiation, dexamethasone and insulin, or media supplemented with approximately 20% horse serum, can be used. Adipocyte differentiation can be detected by examination with light microscopy, staining with oil-red, or detection of lipoprotein (←I'm not sure of the spelling of this) lipase (LPL), adipocyte lipid-binding protein (αP2), or peroxisome proliferator-activated receptor gamma (PPAR). Adipocytes can be used for the treatment of Type II diabetes, and in reconstructive or cosmetic surgery, e.g., for breast reconstruction after mastectomy, or for reshaping tissue lost as a result of other surgery.

To induce skeletal muscle cell differentiation, progenitor cells can be treated with 5-azacytidine in expansion medium for a period, and then transferred to LTC medium. Differentiation can be confirmed by detecting sequential activation of Myf-5, Myo-D, Myf-6, myogenin, desmin, skeletal actin and skeletal myosin, either by immunohistochemistry or Western blot analysis. Smooth muscle cells can also be induced by culturing progenitors in serum-free medium, without growth factors, supplemented with high concentrations of platelet-derived growth factor (PDGF). Terminally differentiated smooth muscle cells can be identified by detecting expression of desmin, smooth muscle specific actin, and smooth muscle specific myosin by standard methods. Cardiac muscle differentiation can be accomplished by adding basic fibroblast growth factor (bFGF) to the standard serum-free culture media without growth factors.

It will thus be appreciated that the progenitor cells of the present invention, their expanded equivalents and their differentiated progeny can be used in cell replacement therapy and/or gene therapy to treat a variety of conditions. Furthermore, the cells can be manipulated to serve as universal donor cells for cell and gene therapy to remedy genetic or other diseases. Particularly useful as donor cells are those progenitors that express neither class of HLA antigen, and which therefore avoid NK-mediated killing when transplanted.

It will be appreciated that cells provided by the present invention can be used to produce tissues or organs for transplantation. Oberpenning, et al. (Nature Biotechnology (1999) 17: 149-155) reported the formation of a working bladder by culturing muscle cells from the exterior canine bladder and lining cells from the interior of the canine bladder, preparing sheets of tissue from these cultures, and coating a small polymer sphere with muscle cells on the outside and lining cells on the inside. The sphere was then inserted into a dog's urinary system, where it began to function as a bladder. Nicklason, et al., Science (1999) 284: 489-493, reported the production of lengths of vascular graft material from cultured smooth muscle and endothelial cells.

Other methods for forming tissue layers from cultured cells are known to those of skill in the art (see, for example, Vacanti, et al., U.S. Pat. No. 5,855,610). These methods can be especially effective when used in combination with cells of the present invention, which have a broad range of differentiation.

For the purposes described herein, either autologous or allogeneic progenitors of the present invention can be administered to a patient, either in differentiated or undifferentiated state, genetically altered or unaltered state, by direct injection to a tissue site, systemically, with an acceptable matrix, or in combination with a pharmaceutically acceptable carrier.

The cells can be provided as frozen stocks, alone or in combination with prepackaged medium and supplements for their culture, and can be additionally provided in combination with separately packaged effective concentrations of appropriate factors to induce differentiation to specific cell types. Alternately, the cells can be provided as frozen stocks containing cells induced to differentiate by the methods described herein above.

In a particular embodiment of the invention, the expanded progenitor cells and particularly the expanded mesenchymal progenitors are utilized in bone therapy. To this end, the cells can be delivered as such or together with a suitable matrix, such as a liquid or gelatinous material, by injection or applied as a paste to a site at which bone formation is desired. Alternatively, the cells can be placed ex vivo in a differentiation environment, exemplified by the CFU-O conditions described herein, and then transplanted to the intended site when their differentiation to bone tissue has reached an appropriately mature stage.

Other embodiments of the invention will be apparent from the following disclosure of experimental procedures and results.

Harvest of Human Bone Marrow-Derived Cells

Human bone marrow-derived cells (hBMDC) were obtained from consenting normal donors (ages 18-55). The cells were fractionated on Ficoll-Paque™ (Sigma) density gradient run at 1750 rpm for 45 minutes at room temperature. Cells were isolated from the gradient interface and were washed twice with Iscove's medium supplemented with 2% heat inactivated fetal calf serum (FCS) before addition to the myeloid long-term culture (LTC) medium. This medium contains a-medium supplemented with 12.5% (FCS), 12.5% horse serum, 0.1 mM B-2-mercaptoethanol, 2 mM 1-glutamine, 0.16 mM 1-inositol and 0.016 mM folic acid (medium referred to as MyeloCult™ and is available from StemCell Technologies (SCT), Inc, Va, BC, Canada).

It will be appreciated by those skilled in the art that the non-hematopoietic progenitor cells may also be derived from human umbilical cord or other tissues that have been shown to contain cells capable of exhibiting a similar developmental capacity to the bone marrow derived cells, e.g., stromal and mesenchymal, potential that can be expanded in suspension and under the appropriate culture conditions.

Also, experimental work along the lines noted below has revealed that similar results can also be achieved when extracted human bone marrow cells are first enriched for parenchymal progenitors before being subjected to fractionation, for instance by the Ficoll-based process just described. Suitable enrichment techniques are those in which the extracted cells are depleted of at least one hematopoietic cell type, such as by processes that utilize antibodies to subtract cells bearing surface markers characteristic of hematopoietic progenitors. One particularly useful technique is the commercially available RosetteSep™ procedure, which is designed to enrich for mesenchymal progenitors.

RosetteSep™ (SCT) contains a combination of mouse and rat monoclonal antibodies purified from mouse ascites fluid or hybridoma culture supernatant. These antibodies are bound to specific bispecific antibody complexes, which are directed against cell surface antigens on human hematopoietic cells (CD3, CD14, CD19, CD38 and CD66b—see below for details in Table 1) and glycophorin A on red blood cells. The mouse monoclonal antibody subclass is $IgG_1$.

TABLE 1

| Surface Marker | Description |
|---|---|
| CD3 | Reacts with the ε chain of the CD3/T-cell antigen receptor (TCR) complex found on 70-80% of normal human peripheral blood lymphocytes and 10-20% of thymocytes. CD3 plays a role in signal transduction during antigen recognition. |
| CD14 | Reacts with a 53-55 kDa glycosylphosphatidylinisitol (GIP) - anchored signal chain glycoprotein expressed at high levels on monocytes. Additionally, CD14 antibody reacts with interfollicular macrophage, reticular dendritic cells and some Langerhans cells. |
| CD19 | Reacts with the 95 kDa type I transmembrane glycoprotein expressed during all stages of B-cell differentiation and maturation, except on plasma cells. CD19 is also present on follicular dendritic cells. It is not found on T cells or on normal granulocytes. CD19 plays a role in regulation of B-cell proliferation. |
| CD38 | Reacts with the 45 kDa type II single-chain transmembrane glycoprotein present on thymocytes, activated T-cells and terminally differentiation B-cells (plasma cells). Other reactive cells include monocytes, macrophage, dendritic cells and some epithelial cells |
| CD66b | Reacts with CD66b, a 100 kDa GPI-linked protein expressed on granulocytes. This molecule was previously clustered as CD67 in the Fourth Human Leukocyte Differentiation Antigen (HLDA) Workshop and renamed CD66b in the Fifth HLDA workshop |

In short, the RosetteSep™ cocktail enriches for mesenchymal progenitor cells by removing the following cells: peripheral blood lymphocytes, peripheral blood thymocytes, monocytes, macrophage, differentiating B-cells, activated T-cells, plasma cells, dendritic cells, some epithelial cells and granulocytes.

RosetteSep™ enrichment for mesenchymal progenitor cells involves adding 50 μl of RosetteSep™ cocktail (available through StemCell Technologies, Canada) per ml of whole bone marrow cells and mixing well, followed by a 20 minute incubation period at room temperature. The sample is then diluted with an equal volume of Phosphate Buffered Saline (PBS)+2% FBS and then mixed gently. The diluted sample is layered on top of density medium (Ficoll-Paque™) while minimizing mixing of the density medium and sample. The tube is centrifuged for 20 minutes at 1750 rpm at room temperature, with the brake off. The enriched cells are located at the plasma interface and are removed.

Initiation of Stirred Suspension Culture

A 100-ml stirred suspension spinner flask (catalogue #: 1965-0010, Bellco, Vineland, N.J.) was used. The flasks were siliconized (Sigma) prior to use to prevent the attachment of adherent cells. Suspension cultures were initiated with approximately $5 \times 10^5$ to $1 \times 10^6$ cells/ml in LTC medium, either with or without the addition of various soluble factors such as 2 ng/ml of highly purified recombinant human interleukin 3 (rhIL-3) (Stem Cell Technologies, VA, Canada), 10 ng/ml of highly purified recombinant human Steel Factor (rhSF) (also referred to interchangeably as stem cell factor, or SCF) (Stem Cell Technologies) or 10, 20 or 30 ng/ml of human recombinant platelet derived growth factor (rhPDGF) (Sigma). Cultures were maintained at 37° C. in humidified atmosphere of 5% $CO_2$ in air with constant stirring at 40 rpm. After 5, 10, and 20 days, half the medium or 7, 14 and 21 days one third the medium was replaced with fresh LTC medium (with or without cytokine addition as at the start). Cell counts and functional assays were performed using the cells at each medium change. Viable cell numbers were determined by trypan blue exclusion using a hemocytometer at input and all subsequent time points. The numbers were recorded to demonstrate the extent of cell expansion in suspension.

Static cell cultures were also run, as a control for stirred suspension cultures.

Initiation of Static Cell Cultures (as Controls for Stirred Suspension Bioreactors)

Static cell cultures (Static Control I) are initiated in T-75 $cm^2$ flask to function as controls for stirred suspension bioreactor experiments. Each flask is initiated with the same concentration of cells (i.e. $1 \times 10^6$ cells/ml) as its parallel stirred suspension bioreactor culture. At 7, 14, and 21 days, one third of the suspension cells, including the media and one third of the adherent cells, detached by 0.01% trypsin treatment, are removed and fresh LTC media with or without the addition of soluble factors is replaced as at the start. Both the suspension and adherent cells recovered from the medium change are counted and analyzed by flow cytometry while only the adherent cells are used in initiating progenitor assays. The remaining two-thirds of the cell culture (with fresh medium) is inoculated into a new T-75 $cm^2$ flask.

Conventional Static Cell Cultures

Conventional static cell culture (Static Control II) experiments were initiated with $1 \times 10^6$ cells/ml in T-75 $cm^2$ flasks, suspended in MesenCult™ medium (SCT) and serial passaged (1:2 split) at 80% confluency. The medium was exchanged 3 times a week. Cultures were maintained at 37° C. in humidified atmosphere of 5% $CO_2$ in air. Cell counts and progenitor assays were performed using the cells at each time point.

A) Functional Assays

CFU-F Assay

The CFU-F assay was used to evaluate the number of marrow mesenchymal cell precursors in cultures maintained in suspension by continuous stirring and the possible effect of the added cytokines on effecting output CFU-F colony numbers and cell composition. CFU-F numbers were determined using a modified version of the method described by Castro-Malaspina et al., 1980. Although having the same essential minerals/vitamins and serum as previously described, the present protocol utilized the medium described below, supplemented with 10% antibiotic solution. The cell suspension obtained from weekly medium changes was washed in Iscove's medium containing 2% FCS (Stem Cell Technologies, VA, Canada). Following centrifugation, the appropriate cell number was resuspended in MesenCult™ medium (Available through SCT and contains fetal bovine serum (10%) in McCoy's 5A medium (modified) supplemented with L-glutamine (2 mM)). The cells were plated at $1 \times 10^4$ cells/$cm^2$ suspended in MesenCult™ medium and then incubated without being perturbed for 14 days. After 2 weeks, the media was removed and the dishes were fixed and stained with α-naphthyl acetate esterase followed by a counterstain with Hematoxylin Solution (Sigma). Adherent colonies containing greater than 50 cells with fibroblastic-like morphology were counted at ×10 magnification.

Bone Nodule Assay (CFU-O)

The cell suspension obtained at weekly medium change was placed in a bone nodule assay determine the capacity of the bioreactor-derived cells to form mineralized nodular areas and to calculated the number of colony forming unit—osteogenic (CFU-O) progenitors. Following the wash and centrifugation steps, the pellet was resuspended in bone forming medium containing α-minimal essential medium, 15% fetal bovine serum by volume, 10% antibiotic solution by volume, and 1% of dexamethasone ($10^{-8}$ M) and L-ascorbic acid (50 μg/ml) by volume and plated on tissue culture polystyrene dishes at a cell seeding density of $1 \times 10^4$ cells/$cm^2$. Once a morphologically identifiable change in cell shape was observed using a phase contrast microscope, β-glyercophosphate at a concentration of 3.5 mM was added to the culture. Each week until termination the flasks were re-fed with fresh medium. The cultures were maintained until such time as mineralized nodular areas were observed after which the cultures were fixed and prepared for analysis.

B) Data Analysis

Tetracycline Stain

Tetracycline (9 μg/ml) was added to the cultures prior to termination. At termination, the cells were fixed in Karnovosky's fixative overnight and then viewed by UV-excited fluorescence imaging for tetracycline labeling of the mineral component of the nodular areas.

Scanning Electron Microscopy (SEM)

Representative samples of bone nodule cultures were prepared for SEM by first placing them in 70%, 80%, 90% and 95% ethanol for 1 hour, followed by immersion in 100% ethanol for 3 hours. They were then critical point dried. A layer of gold approximately 3 nm layer was sputter coated with a Polaron SC515 SEM Coating System onto the specimens, which were then examined at various magnifications in a Hitachi S-2000 scanning electron microscope at an accelerating voltage of 15 kV. The images generated were used to demonstrate the presence of morphologically identifiable bone matrix.

Flow Cytometry Analysis and Phenotyping

Cell surface expression of a variety of markers were analyzed on the cell suspension at time points noted in FIG. 6. The analyzed markers included CD34, CD45, SH2, SH4 and STRO-1. For the analysis, single-cell suspensions of $1 \times 10^5$ cells/ml were prepared and incubated with saturating concentrations of the following conjugated monoclonal antibodies either alone or for 2-colour experiments: CD34-FITC (fluroescein isothyocynanate), CD45-PE (phycoerythrin), CD45-FITC, SH2-FITC and SH4-FITC for 30 minutes at 4° C. or on ice. The cell suspension was washed twice with PBS+2% FBS prior to the addition of the viability stain 7 AAD.

The procedure for the STRO-1 antibody stain involved resuspending the cell suspension ($1 \times 10^5$ cells) in 200 μl of saturating concentrations of the mouse IgM monoclonal antibody STRO-1 for 30 minutes at 4° C. or on ice. This step was preceded with blocking the cell suspension with 1% human, goat and mouse sera for 10 minutes. The cells were then washed twice with PBS containing 2% FBS before the addition of 3 μl/$10^5$ or 100 μl of PE-conjugated rat anti-mouse IgM monoclonal antibody (BD Biosciences, CA). Cell suspensions were washed twice with PBS+2% FBS and then 7 AAD was added to the final suspension. Cell analysis was employed using Becton Dickinson Immunocytometry System. Appropriate controls included matched isotype antibodies to establish positive and negative quadrants, as well as appropriate single colour stains for compensation. For each sample, at least 10 000 list mode events were collected.

Embodiments of the present invention are described in the following specific examples. It will be understood these examples are exemplary and are not intended to limit the scope of the invention in any way.

EXAMPLE 1

Total Cell and Colony Forming Unit (CFU) Expansion

Figure 1B:
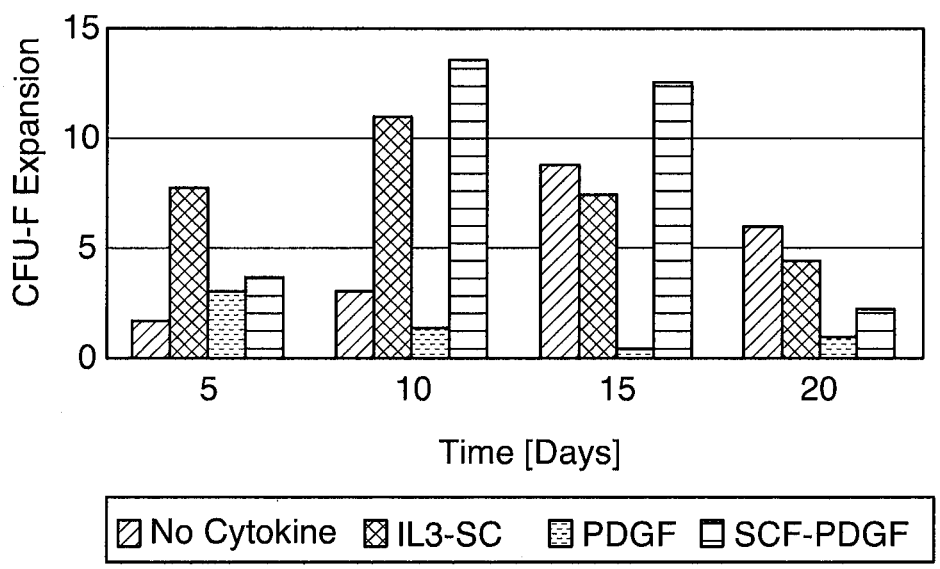
FIG. 1B shows the expansion profile of the colony forming units (CFU) generated from the cells maintained in each treatment group upon plating in a CFU-F assay.

Stirred suspension bioreactors were initiated with $8.5 \times 10^6$ cells suspended in Myelocult™ medium for 20 days. Each bioreactor received a different treatment that included no cytokines, SCF+IL3, SCF+PDGF, or PDGF. At days 5, 10, 15 and 20, half the medium was removed and replaced with fresh medium containing the appropriate cytokine supplementation. The cells were counted and plated in a CFU-F and bone nodule assay at a cell seeding density of $1 \times 10^4$ cells/$cm^2$. FIG. 1A is a graphic representation illustrating the change in total cell number with time, relative to input cell numbers, from human bone marrow-derived cells maintained in a stirred suspension bioreactor. FIG. 1B shows the expansion profile of the colony forming units (CFU) generated from the cells maintained in each treatment group. The colonies generated from the expanded cell population were normalized relative to the numbers of colonies generated from the input cell population. It is evident from these results that the no cytokine and SCF+IL3 treatment groups support a net expansion of total cell numbers and the same groups show a 5-10 fold expansion in CFU-F numbers by Day 15.

Figure 1C:
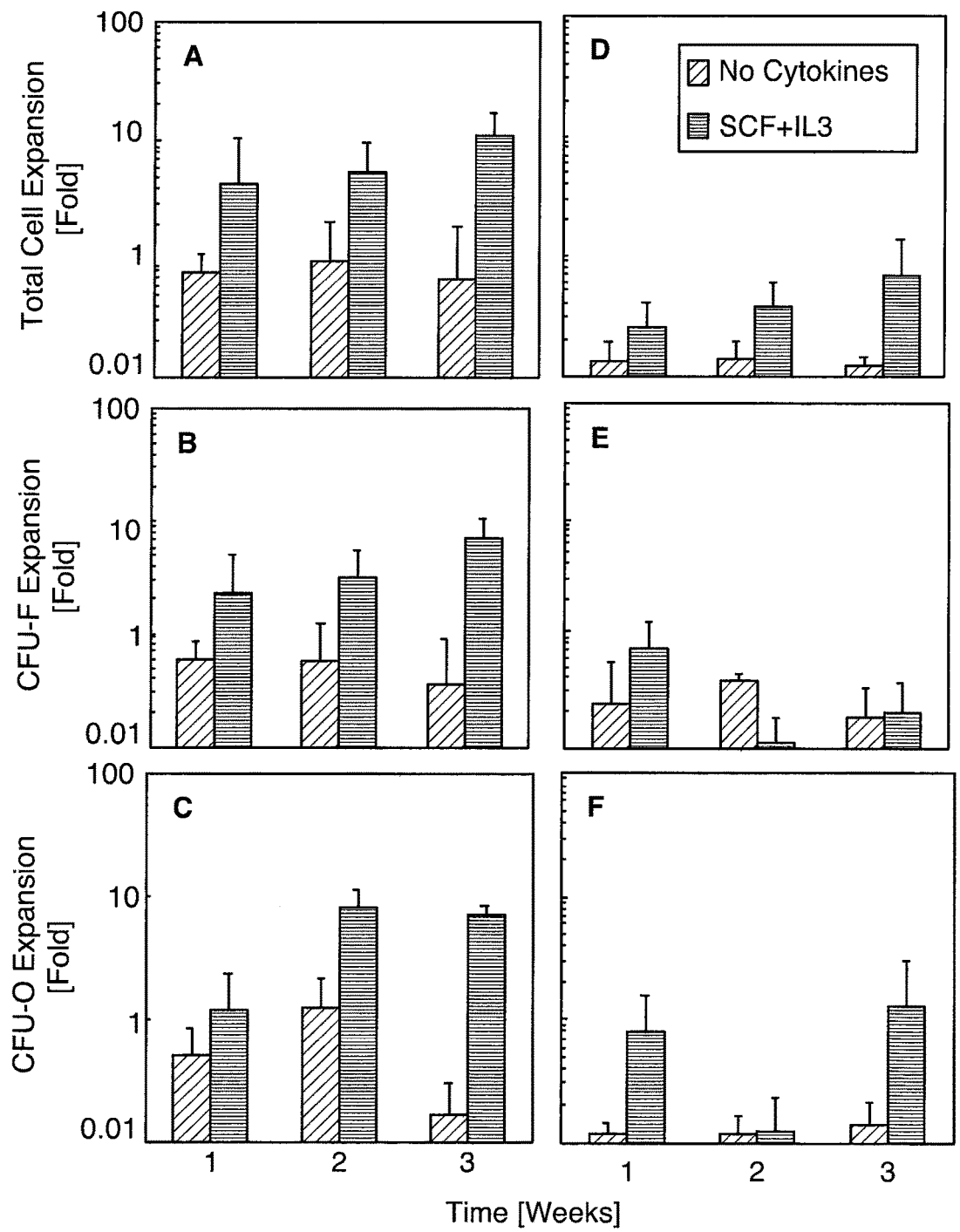
FIG. 1C is a graphical representation of total cell (panels A,D), CFU-F (B,E) and CFU-O (C,F) expansion calculated from cells grown in stirred suspension bioreactors (A-C) and static control cultures (D-F). Bars represent the mean of three different experiments±standard deviation (see also FIG. 8).
Figure 1D:
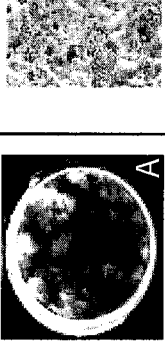
FIG. 1D shows various types of differentiated cells induced from the parenchymal progenitor cell population, grown in the presence of defined cytokine cocktails. The cytokine concentrations used were 10 ng/ml (stem cell factor) (SCF), 2 ng/ml interleukin-3 (IL3), 100 ng/ml macrophage colony stimulating factor (MCSF), and 30 ng/ml platelet-derived growth factor (PDGF). In addition to bone nodule formation detected by UV-fluorescence excitation of tetracycline labeled cultures (A) (Week 1 SCF+IL3 bioreactor-derived cells cultured in osteogenic conditions shown here), cells containing fat globules (B) (FW: 2.55 mm) formed in bone nodule assays that were initiated with cells removed from selected bioreactor culture treatments (tabular results). Image (C) shows typical cells that grew in a CFU-F assay that were initiated with cells removed from stirred suspension bioreactors of the SCF+IL3 treatment group after 1 week (FW: 2.85 mm). CFU-F cultures were stained with α-naphthyl acetate esterase followed by a counterstain with Hematoxylin solution at 2 weeks. Image (D) (FW: 2.85 mm) shows the typical cells that comprised CFU-F assays that were initiated with bioreactor-derived cells cultured in the presence of PDGF.
Figure 1D:
Figure 1D:
Figure 1D:
Figure 2:
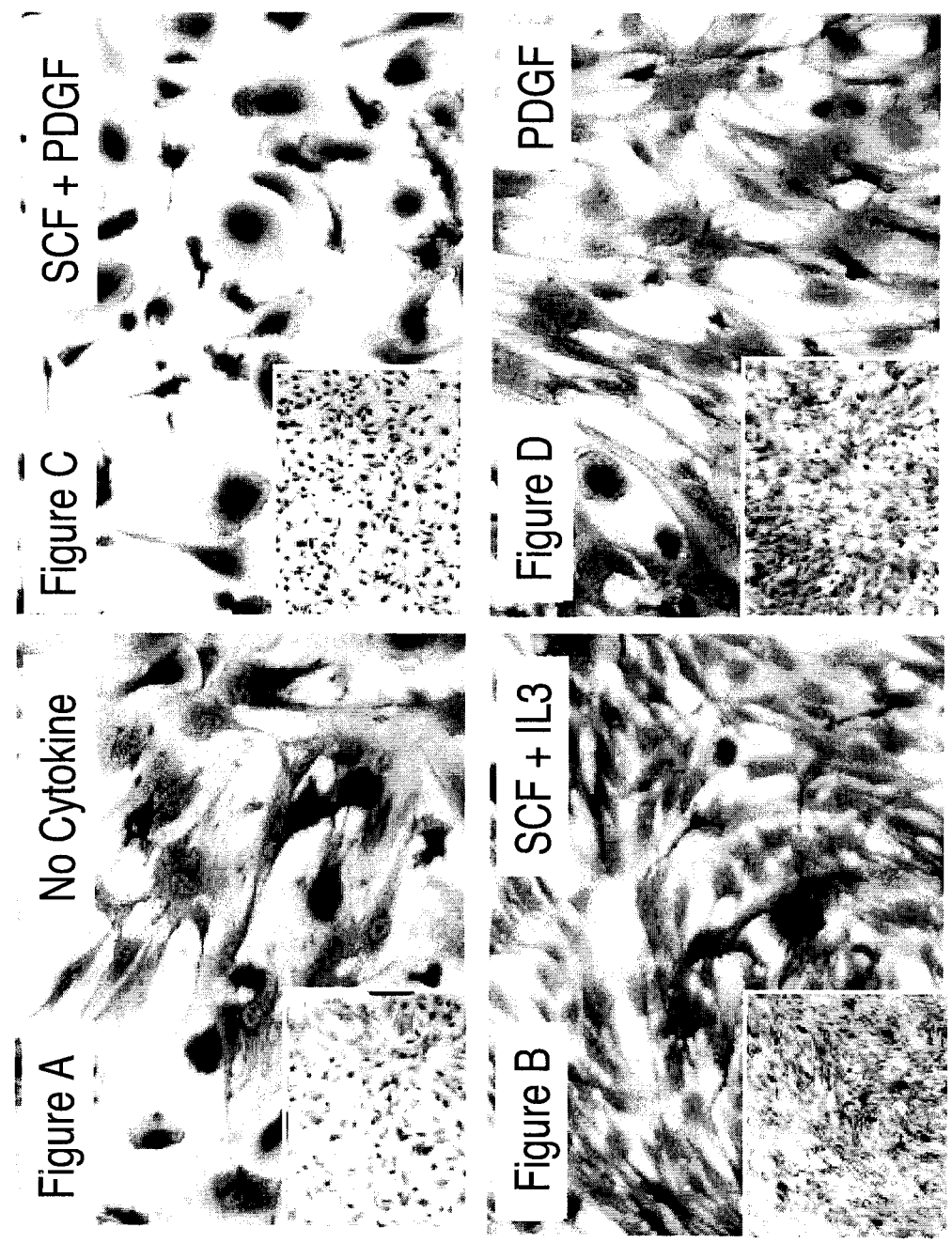
FIGS. 2A-2D are optical micrographs taken of CFU-F cultures of suspension cells isolated from bioreactors at Day 5 with differing combinations of cytokines.
FIGS. 2E-2H are CFU-F assay results of cells removed from suspension bioreactors at Day 20 with differing combinations of cytokines.
Figure 2:
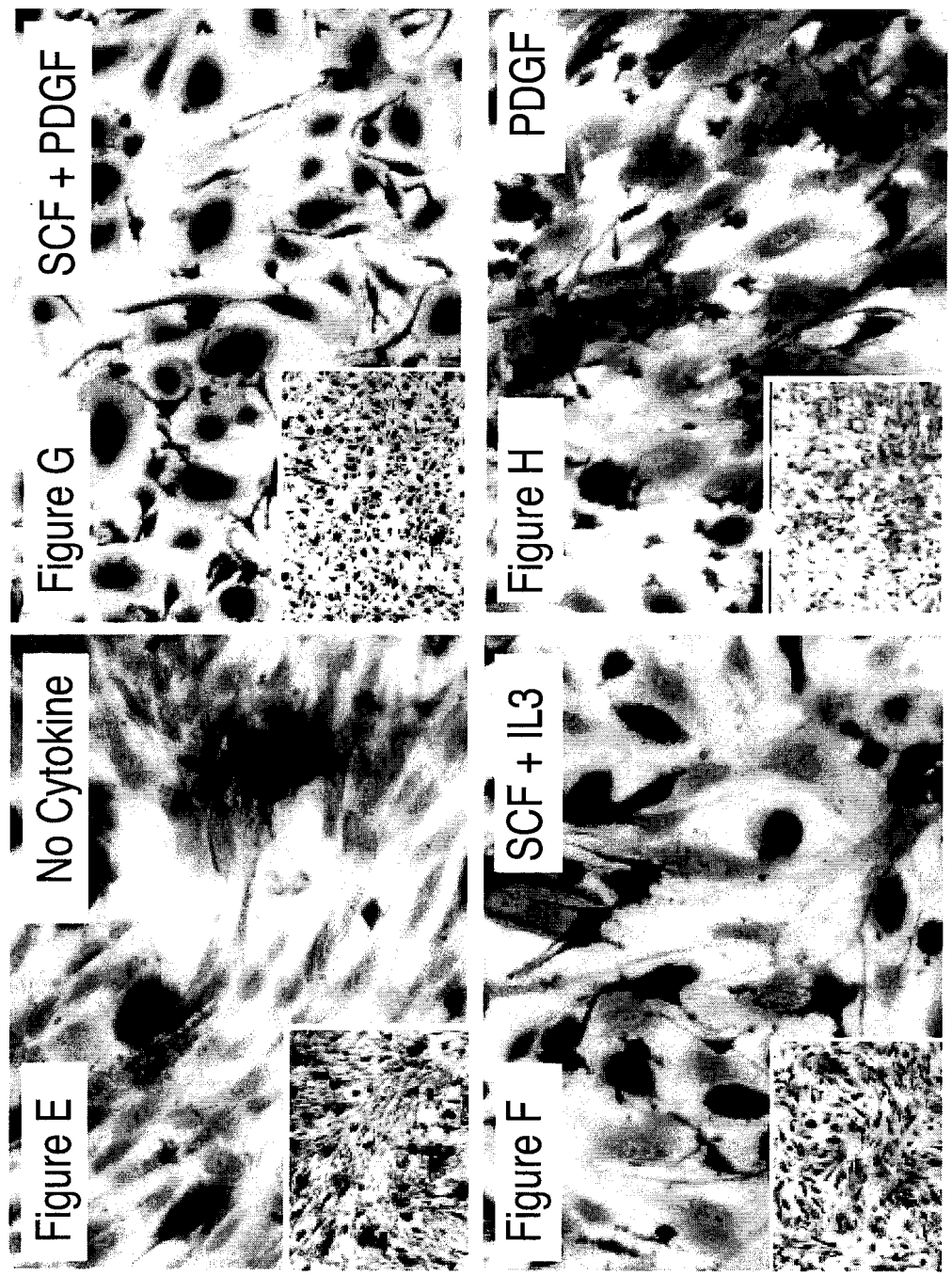
Figure 3:
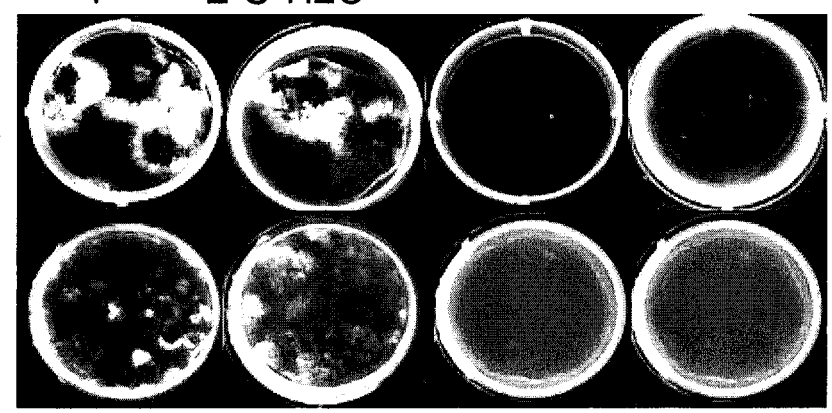
FIGS. 3A, 3B, 3C and 3D depict tetracycline labeled osteogenic cultures of Day 5 and Day 10 suspension cells maintained in the presence of various cytokines. Mineralized nodular areas first appeared after 3 weeks and cultures were terminated at 5 weeks. Fluorescence intensity corresponded to tetracycline that had chelated to the mineralized areas. The images in (A-B) reveal tetracycline signals that corresponded to nodule-like structures that formed from cells that were removed, at 5 and 10 days from suspension bioreactors supplemented with various cytokine cocktails. All bone nodule assays were initiated with $1\times10^4$ cells/cm$^2$. The tetracycline signal from each bone nodule culture initiated with cells derived from bioreactors experiments were quantified using the ChemiImager 5500 software (Alpha Innotech Corporation, San Leandro, Calif.)
FIG. 3E illustrates the expansion of CFU-O progenitors detected as bone nodule colonies over the time period in those conditions presented in FIGS. A-D.
Figure 3:
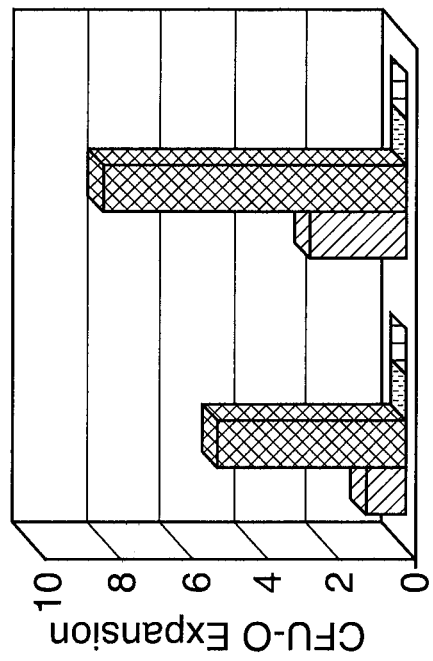
Figure 3:
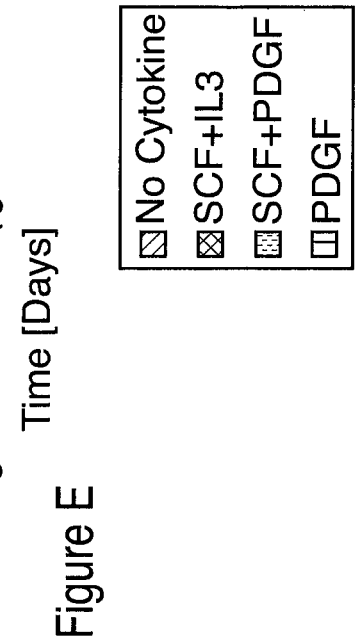

Similarly, FIG. 1C shows the advantage of stirred suspension bioreactors over static control cultures, in expanding the progenitor cell population, and importantly, in producing mesenchymal progenitor cells that differentiate into fibroblast and bone cell colonies. FIG. 1D shows the morphology of cells differentiated from the expanded progenitors.

Figure 8:
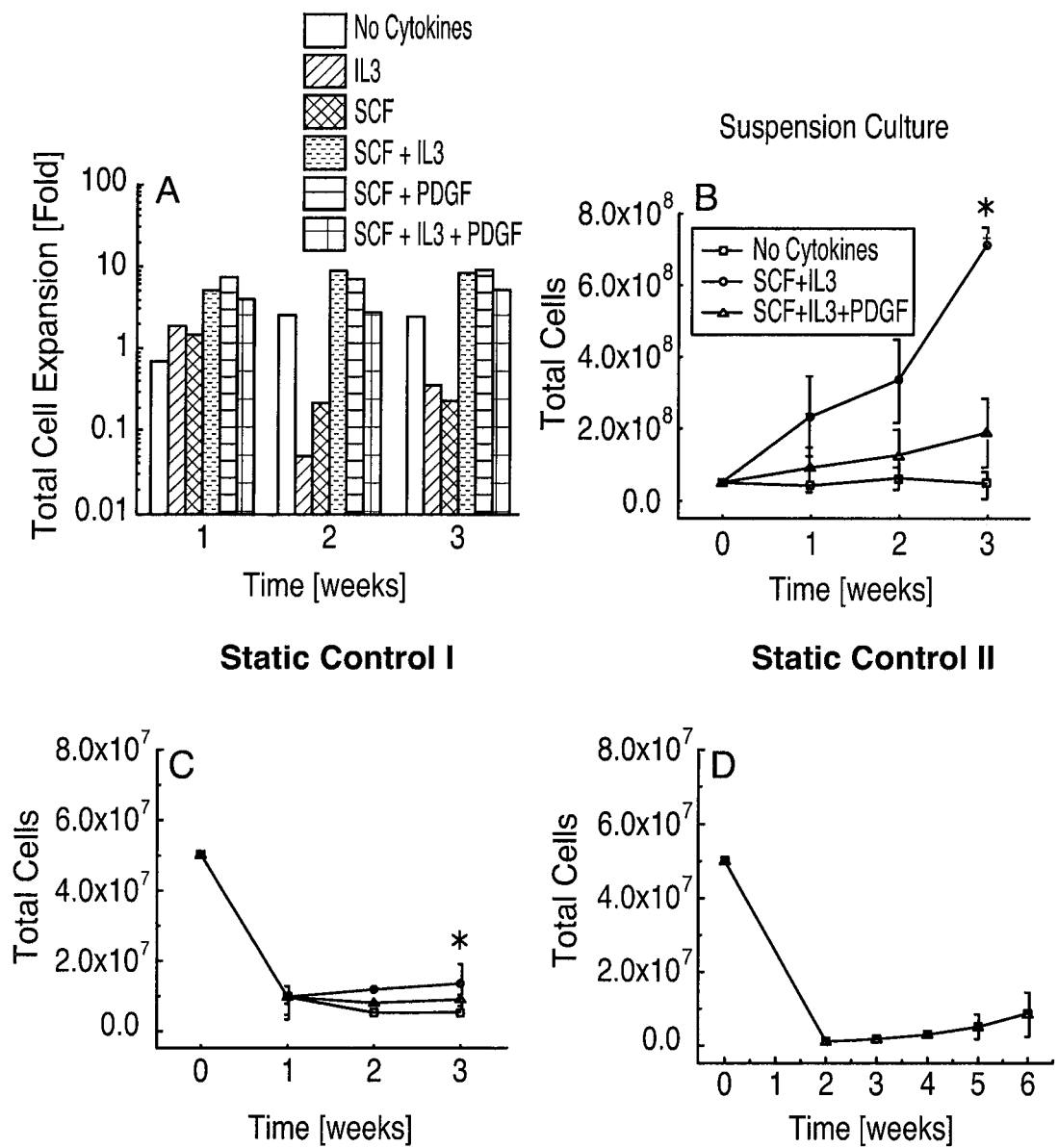
FIG. 8 reveals total cell expansion in stirred suspension bioreactors as a function of cytokine supplementation. (A) A preliminary study (n=1 for each treatment group) investigating the effect of stem cell factor (SCF, 10 ng/ml), interleukin-3 (IL3, 2 ng/ml) and platelet-derived growth factor (PDGF-BB, 30 ng/ml), alone or in combination, on total cell expansion. Cultures that achieved a 5-fold or greater increase in total cells by 3 weeks were further analyzed. (B) demonstrates the extent of cell growth attained in 3 weeks through suspension culturing as of function of cytokine addition. Two types of static control experiments were performed: Static Control I (C) and II (D). Both controls were run in parallel to bioreactor cultures. The first type of control (Static Control I) was designed to function as a control for bioreactor cultures and therefore, was initiated with the same number of cells, suspended in the same growth medium and a one-third medium exchange (including both adherent and suspension cells) was performed weekly. Static Control II involved initiating cultures also with the same number of cells as the bioreactor cultures; however, the cultures were passaged at ~80-90% confluency and then split 1:2. (C and D) represent the extent of cell growth achieved through the two types of static cultures. Note the scale difference on the y-axis in C and D compared to B. Each point represents the mean of 3 independent experiments were the error bars represent S.D. Significant differences ($p<0.05$) in total cells (for both B and C) were observed between the groups at week 3 (denoted with *)

Similarly, FIG. 8 shows the effect on expansion of various cytokine combinations, measured at weekly intervals. It is apparent that, by 3 weeks of culture, certain treatment groups resulted in greater total cell expansion, while others failed to even maintain input cell numbers (FIG. 8A). The groups with cell expansions of greater than 5-fold after 3 weeks of culture were namely the SCF+IL3 and SCF+IL3+ PDGF. To assess the feasibility of using stirred suspension bioreactors to culture bone marrow-derived cells, two different static control experiments were performed in parallel to the stirred suspension bioreactor cultures; Static Control I (FIG. 8C) and Static Control II (FIG. 8D). It is apparent that the total cell growth attained in both types of static culture configurations is minimal compared to the growth that is achieved through suspension culture (FIGS. 8C and D: note the scale difference from 8A).

Figure 9:
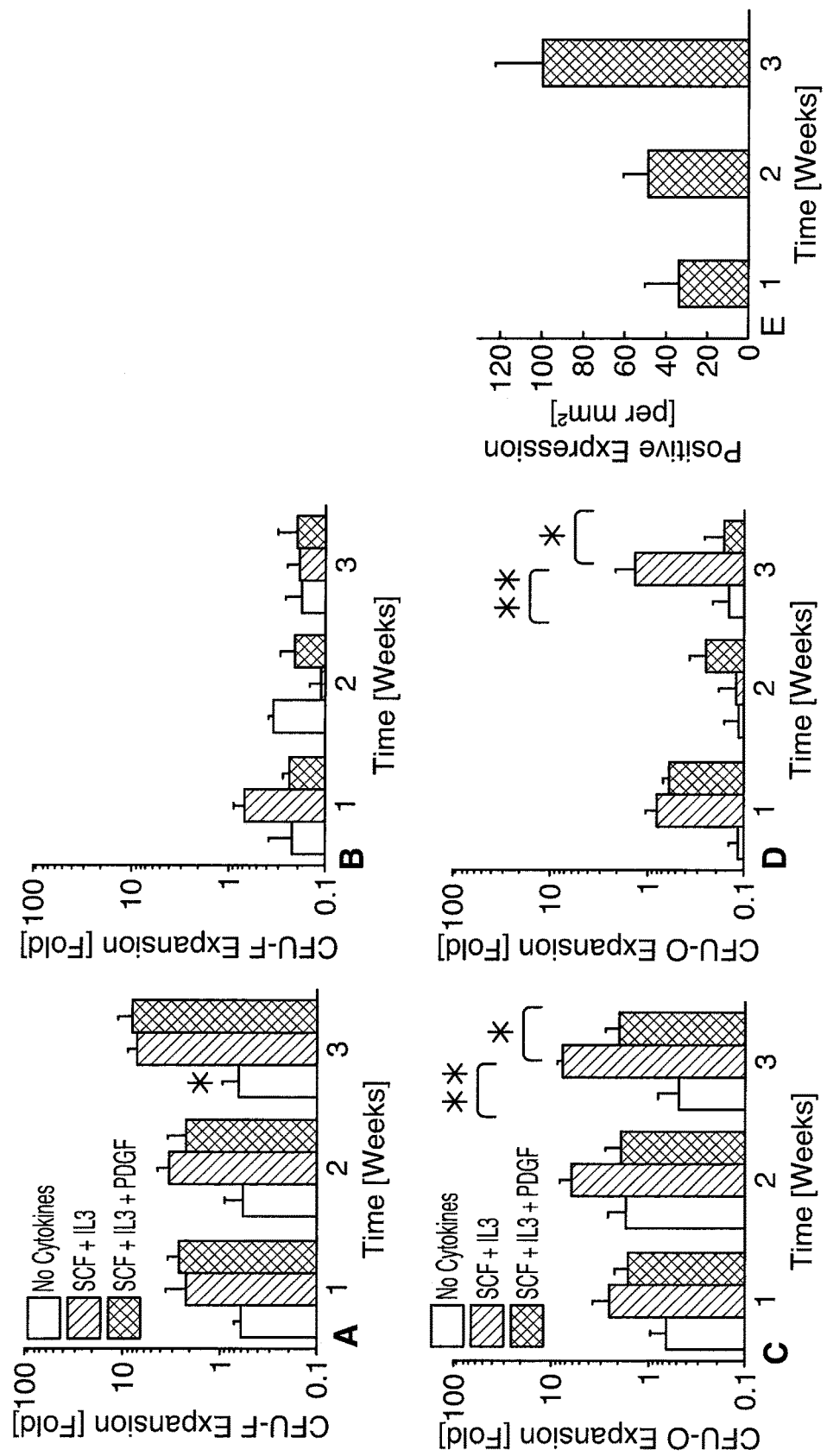
FIGS. 9A and 9B are graphic representations of the fold increase in CFU-F numbers relative to input from cells derived from suspension bioreactor treatment groups and adherent cells removed by 0.1% trypsin treatment from static controls (type 1), respectively. A significant difference ($p<0.05$) was observed in CFU-F expansion between the No Cytokine and the other treatment groups at week 3 (denoted with *) in 9A. Nodular areas were enumerated and used to calculate the fold increase in CFU-O numbers relative to input from cells derived from bioreactor cultures (FIG. 9C) and cells removed from the adherent fraction of static control (type 1) experiments (9D). A significant difference ($p<0.05$) in CFU-O expansion was observed between the No Cytokine and SCF+IL3 treatment group at week 3 (denoted with * and ** between the treatment groups) in 9C and 9D.
FIG. 9E shows a graphical representation of the positive expression associated with NeuN expressing cells of 2-week old CFU-F cultures that were initiated with cells removed from a SCF+IL3+PDGF supplemented bioreactor at 1, 2 and 3 weeks. The cultures were incubated with mouse anti-NeuN monoclonal antibody (MoAb) and positive expression was detected as a fluorescence signal above background using an anti-mouse MoAb conjugated to Alexa Fluor 594. Ten random images from each culture treatment group were taken of 2-week old CFU-F cultures that were initiated with 1, 2 and 3-week bioreactor-grown cells. The images were used to quantify the increase in the number of cells expressing NeuN after 1, 2 and 3 weeks of suspension culturing. Each bar represents the results of 30 fields from 3 independent experiments (10 fields per treatment group)±S.D.
Figure 10:
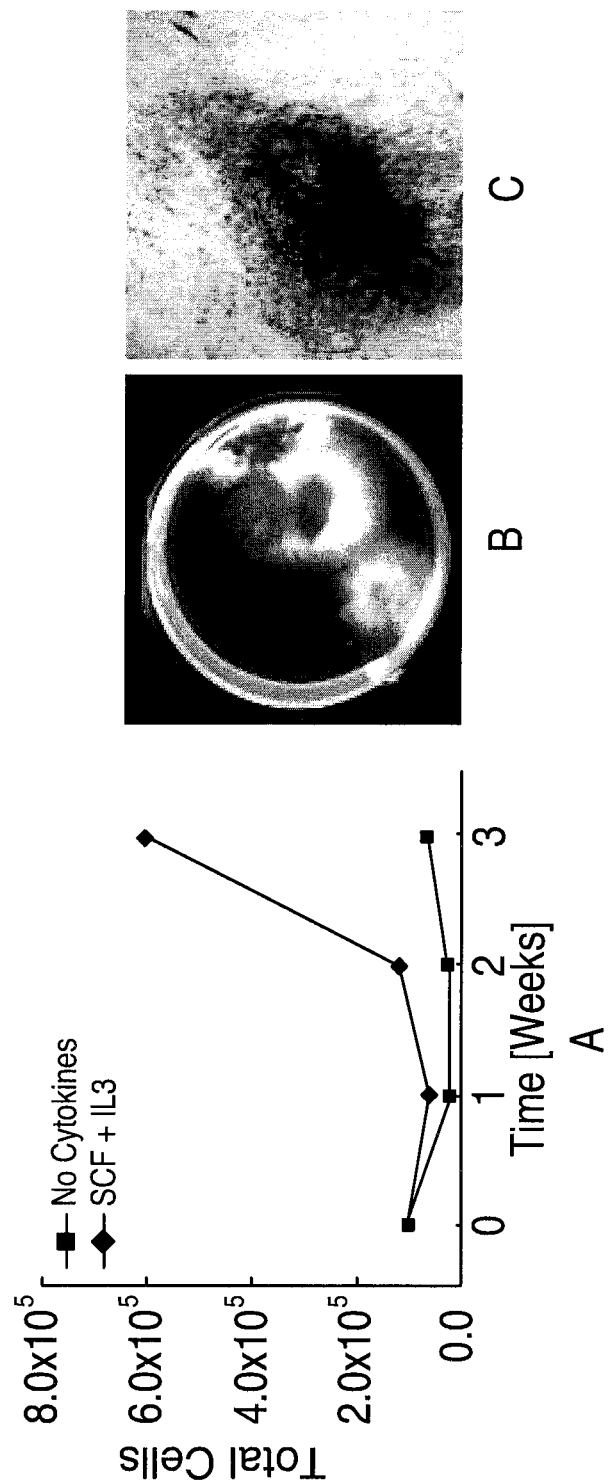

FIG. 9 shows the results of testing the functional capacity of our bioreactor grown cells to form bone matrix and colonies of fibroblast-like cells. Colonies of fibroblast-like cells were enumerated from bioreactor-derived cells inoculated in CFU-F assays and the fold increase in CFU-F numbers were calculated relative to input (FIG. 9A). Tetracycline labeling of bone nodule cultures was used to label the newly formed biological mineral phase of bone and as a method of enumerating CFU-O progenitors to determine the extent CFU-O expansion over the time period studied. FIG.

9C shows a graphic representation of the calculated fold expansion of CFU-O numbers relative to input. SCF+IL3 and SCF+IL3+PDGF supplementation supported a greater CFU-O expansion, where a maximum of 8±1.5 fold increase in CFU-O expansion was achieved in the SCF+IL3 treatment group by 3 weeks. FIGS. 9B and 9D are static control I CFU-F and CFU-0 expansion results. It is apparent that there is a greater extent of these progenitors expansion achieved through suspension culturing. Light micrographs of cells generated in the CFU-F assays of the PDGF-treated cultures suggested, based on morphology, that the cells maybe of neural origin. To test this hypothesis, 2-week old CFU-F cultures initiated with cells grown from bioreactors supplemented with PDGF were incubated with a neural specific marker, NeuN, a neural binding protein[6]. NeuN appeared to localize to the nuclear area of the cell body as seen by an intense staining in this region. NeuN positive cells present in CFU-F assays that were initiated with suspension culture cells that were removed from bioreactors at 1, 2 and 3 weeks clearly increased with time of suspension culture (FIG. 9E).

EXAMPLE 2

Light Micrographs of CFU-F and CFU-O Colonies

FIGS. 2A-D represents light micrographs taken of CFU-F cultures of suspension cells isolated from bioreactors at Day 5. At 14 days, cultures were with stained with a-naphthyl acetate esterase followed by a counterstain with Hematoxylin Solution. FIGS. 2E-2H are CFU-F assay results of cells removed from suspension bioreactors at Day 20. Note the similarity in the cells comprising the colonies from Day 5 and Day 20 suspension cells, with the SCF+PDGF treatment having a strikingly different cell composition and morphology from the rest of the treatment groups.

Light micrographs generated from the CFU-F assays of the SCF+IL-3+PDGF treated cultures indicated that certain cells were of neuronal origin based on morphological characteristics similar to neuron cells (see for instance panel D of FIG. 1D). When immunolabeled for a-tubulin and NeuN, the extent of tubulin expression was observed in what appear to be neurite outgrowths originating from the cell body, while the NeuN positive stain localized in the nuclear area of the cell body. Similar cells were observed in CFU-F cultures from cells removed from the bioreactor cultures at week 2 and week 3.

EXAMPLE 3

Tetracycline Labeling of CFU-O Cultures

Figure 4:
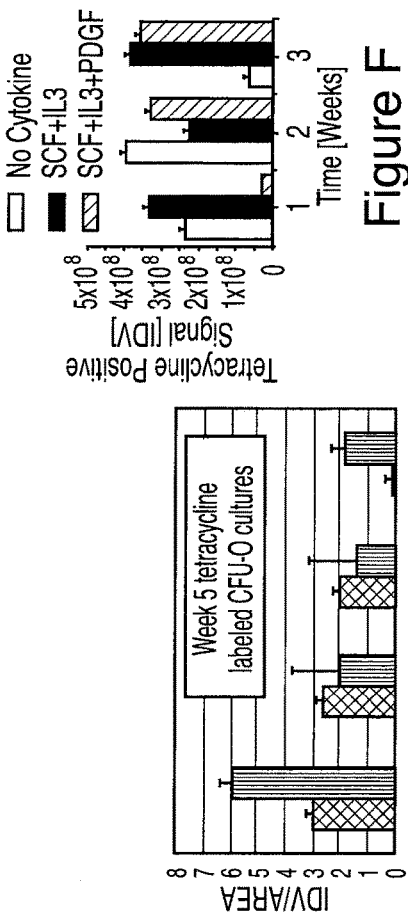
FIGS. 4A and 4B show dark field micrographs of developing nodular areas (3 weeks) generated from cells derived from the no cytokine and SCF+IL3 bioreactor treatment groups after 7 days of suspension culturing.
FIGS. 4C and 4D show no nodular areas associated with the cells retrieved from the SCF+PDGF treatment.
FIG. 4E is a graphical representation showing the tetracycline signal associated with the mineralized areas of FIGS. 3A, 3B, 3C and 3D quantified and normalized to the input signal of bone nodule cultures initiated with cells removed from the culture suspension on day 5 and day 10.
FIG. 4F and 4G are also graphical representation showing the tetracycline signal from each bone nodule culture initiated with cells derived from both bioreactors and static control (type 1) experiments (see FIG. 8 description for static control type I description). Panels F and G reveal the quantitative results, including results with a combination of SCF+IL-3+PDGF, where the tetracycline positive signal is expressed as an integrated density value (IDV). All bone nodule assays were initiated with $1\times10^4$ cells/cm$^2$. Each bar represents the mean tetracycline positive signal from 3 bone nodule cultures±SD for each cytokine conditions.
Figure 4:
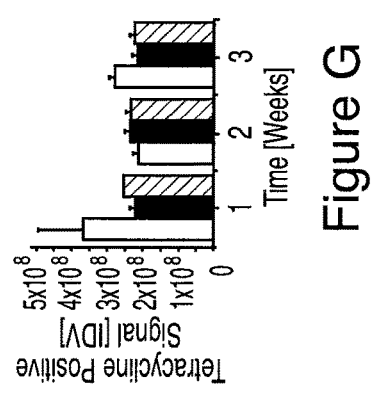
Figure 4:
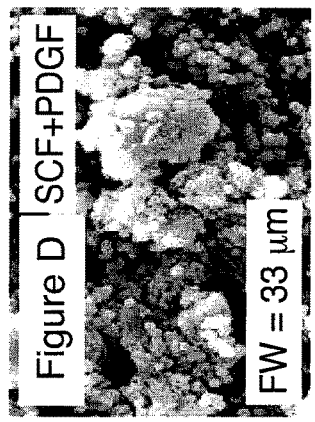
Figure 4:
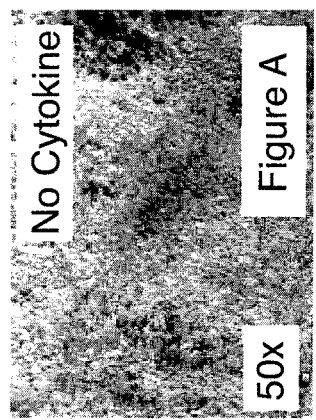
Figure 4:
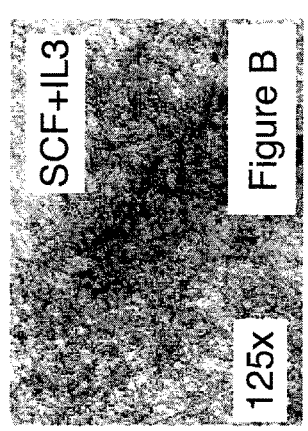
Figure 4:
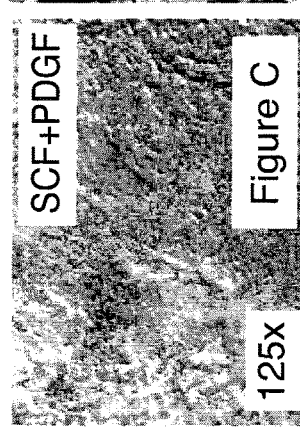

Tetracycline labeling of cultures was used for labeling of the newly formed calcium phosphate associated with the biological mineral phase of bone. The tetracycline labeling of the cultures coincide with the mineralized nodular areas, which is visualized by exposing the cultures to UV light. FIGS. 3A-3D depict tetracycline labeled bone nodule cultures of Day 5 and Day 10 suspension cells maintained in the various cytokine conditions. These images were generated by UV-excited fluorescence imaging. The CFU-O colonies were enumerated by this method and FIG. 4F illustrates the expansion of CFU-O colonies over the time period from the treatment conditions described in FIGS. 3A-D. As can be seen, both the no cytokine and SCF+IL3 treatment groups showed quantifiable levels of expansion where as the SCF+PDGF and PDGF treatment groups did not yield any bone colonies. FIGS. 4A and 4B show dark field micrographs of developing nodular areas associated with the no cytokine and SCF+IL3 groups. FIGS. 4C and 4D show no nodular areas associated with the cells retrieved from the SCF+PDGF treatment (such results were also observed for the PDGF treatment, data no shown). The tetracycline signals associated with the mineralized areas were quantified and normalized to the input CFU-O signal, as shown in FIG. 4E. As can be seen, the SCF+PDGF and PDGF groups show a tetracycline signal, however, this signal is associated with the random deposition of mineral throughout the culture dish, which can be described as dystrophic mineralization. Similar experiments were performed on No Cytokine, SCF+IL3 and SCF+IL3+PDGF suspension bioreactors whereby cells were removed instead at 1, 2 and 3 weeks (FIGS. 4F and 4G). It is apparent that the SCF-IL3 and SCF+IL3+PDGF conditions (4F) resulted in a greater tetracycline signal at 3 weeks when compared to controls (4G).

EXAMPLE 4

SEM and TEM Images of CFU-O Cultures

Figure 5:
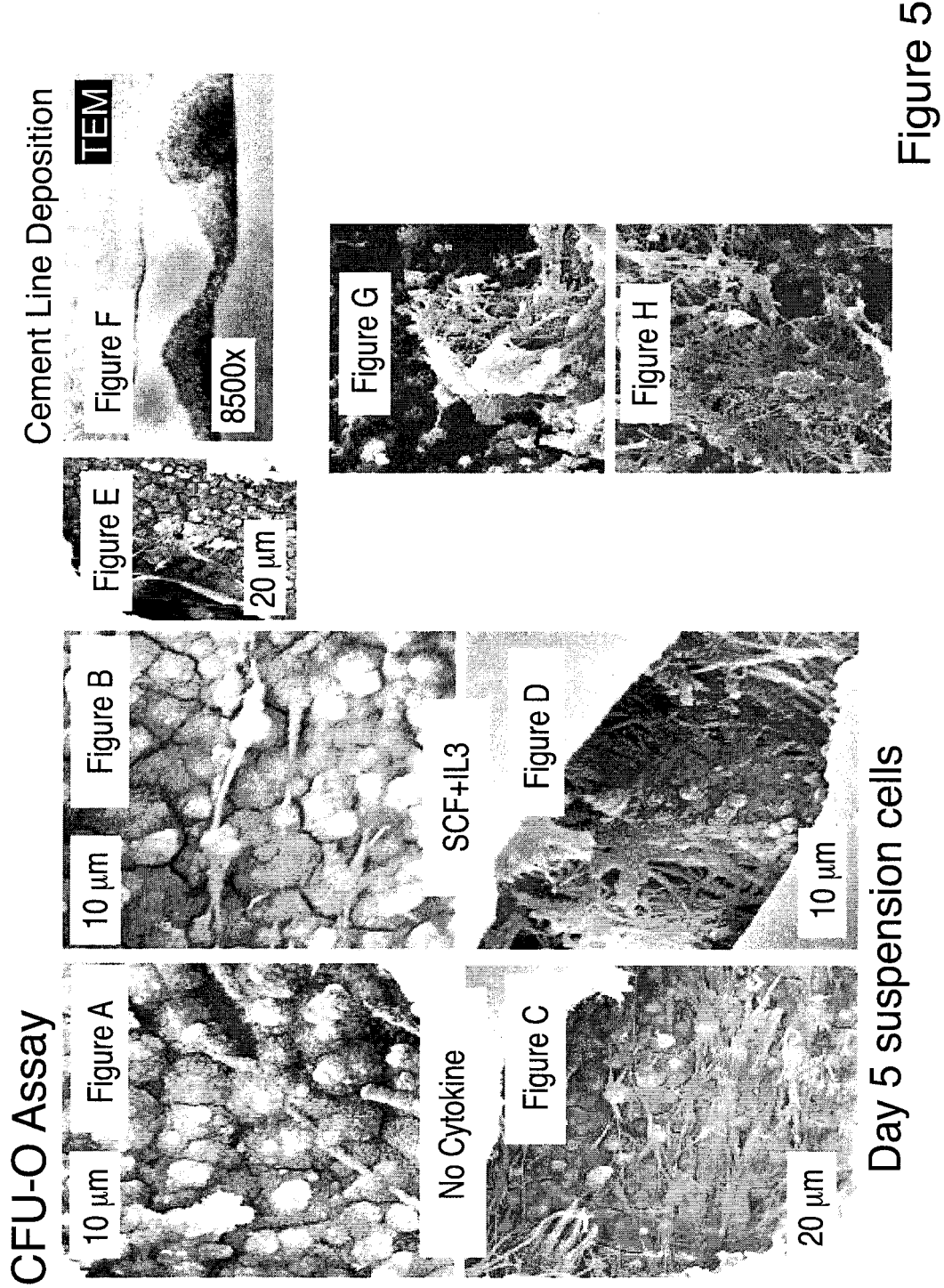
FIGS. 5A-5D are scanning electron microscope (SEM) images taken of bone nodule cultures of Day 5 suspension cells that were grown in the various treatment groups studied.
FIG. 5F is a transmission electron microscope (TEM) image showing that the matrix lining the culture dish comprises globular accretions that form the cement line matrix.
FIG. 5E shows a differentiating osteogenic cell secreting globular accretions forming the cement line matrix.
FIGS. 5G and 5H are images taken from cultures initiated with cells removed from bioreactors after 3 weeks. Field widths (FW: 17 μm for G and H)
Figure 6A:
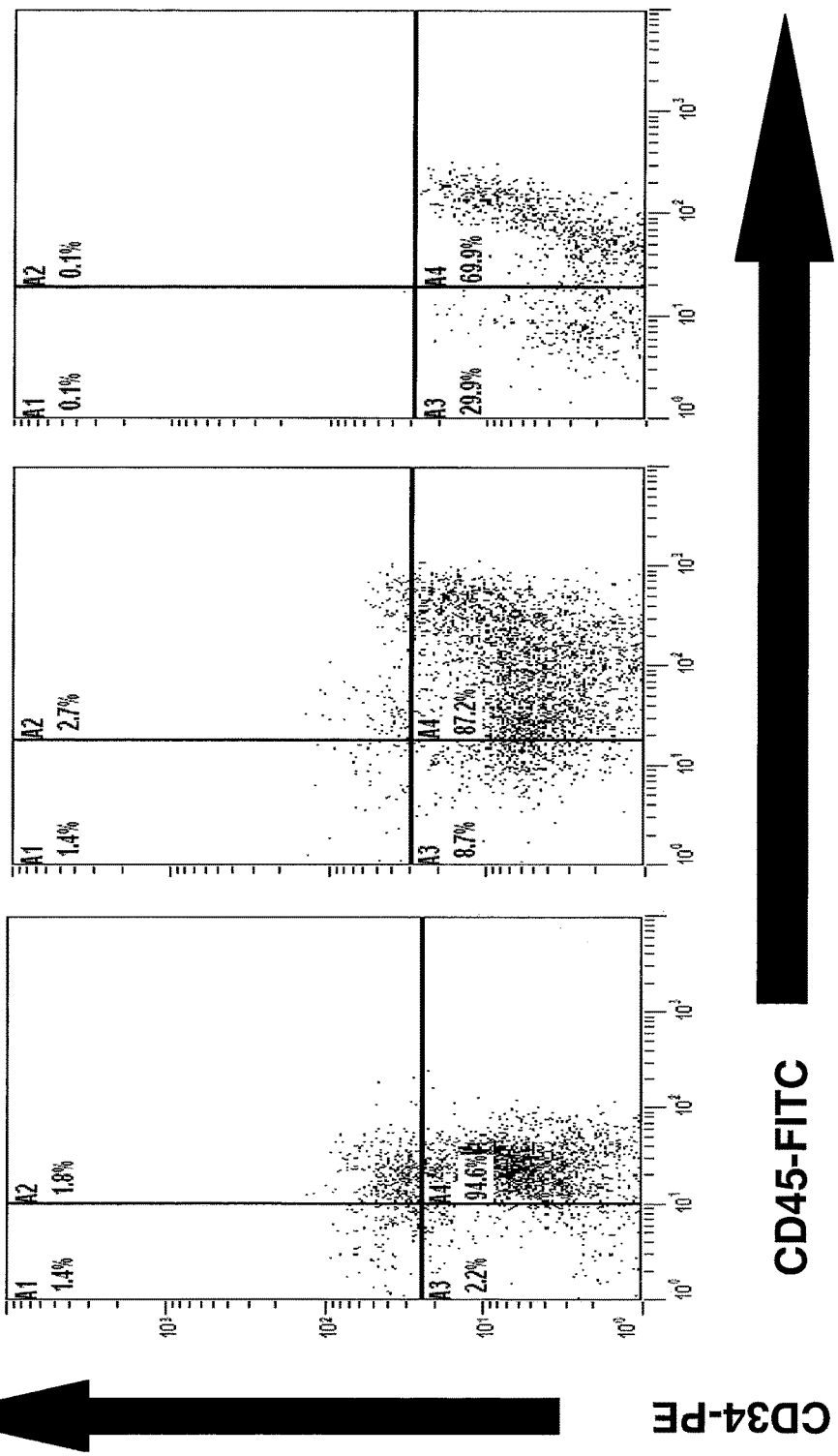
FIG. 6A reveals CD34 and CD45 phenotype and progression over culturing time in the presence and absence of cytokines. The input population contained a 65% CD45 and 0.5% CD34 population.
Figure 6A:
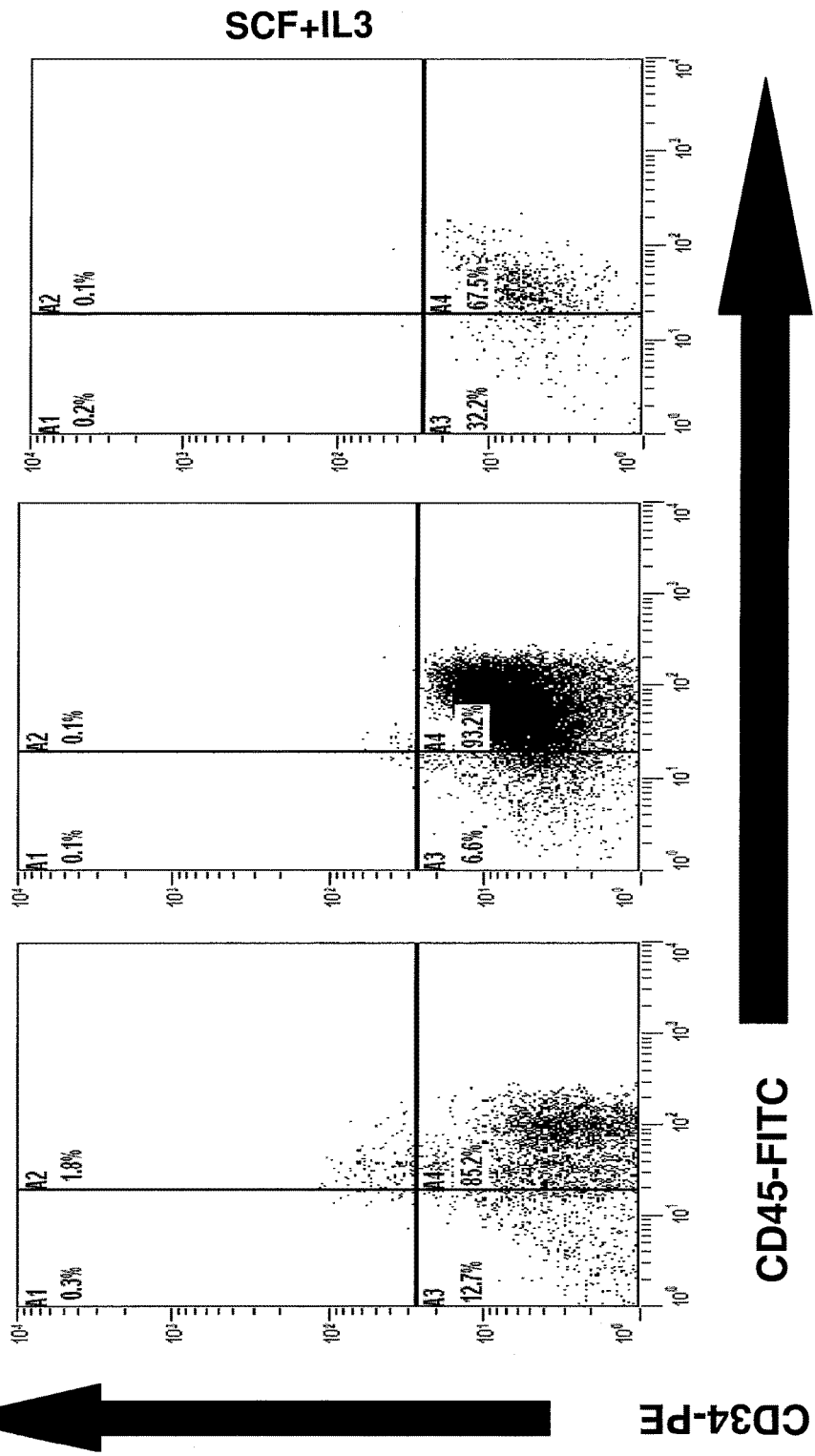
Figure 6B:
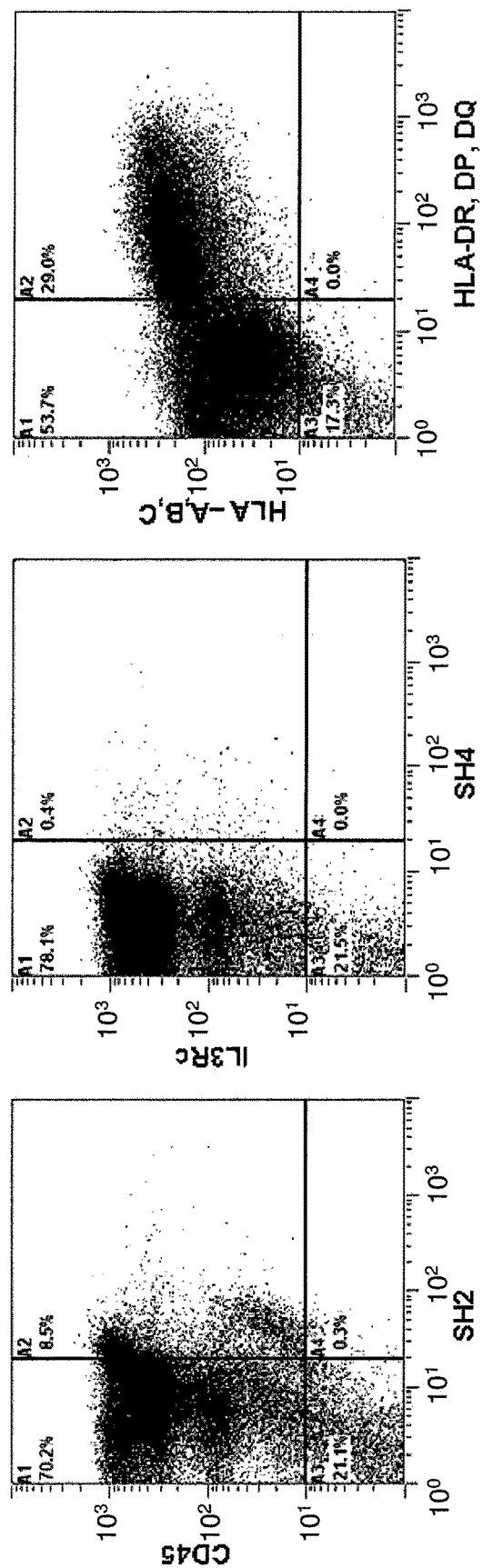
FIG. 6B particularly shows dot plots generated from Ficoll-Paque™ bone marrow incubated with various antibodies against cell surface markers. The dot plots reveal that Ficoll-Paque™ processed human bone marrow contains populations of cells that are CD45$^+$, CD34$^{low}$, CD50$^+$, SH2$^{low}$, SH4$^-$ and STRO-1. The cell population also includes a double negative population (~17%) when incubated with antibodies against HLA-A,B,C and –DP,DQ, DR.
Figure 6B:
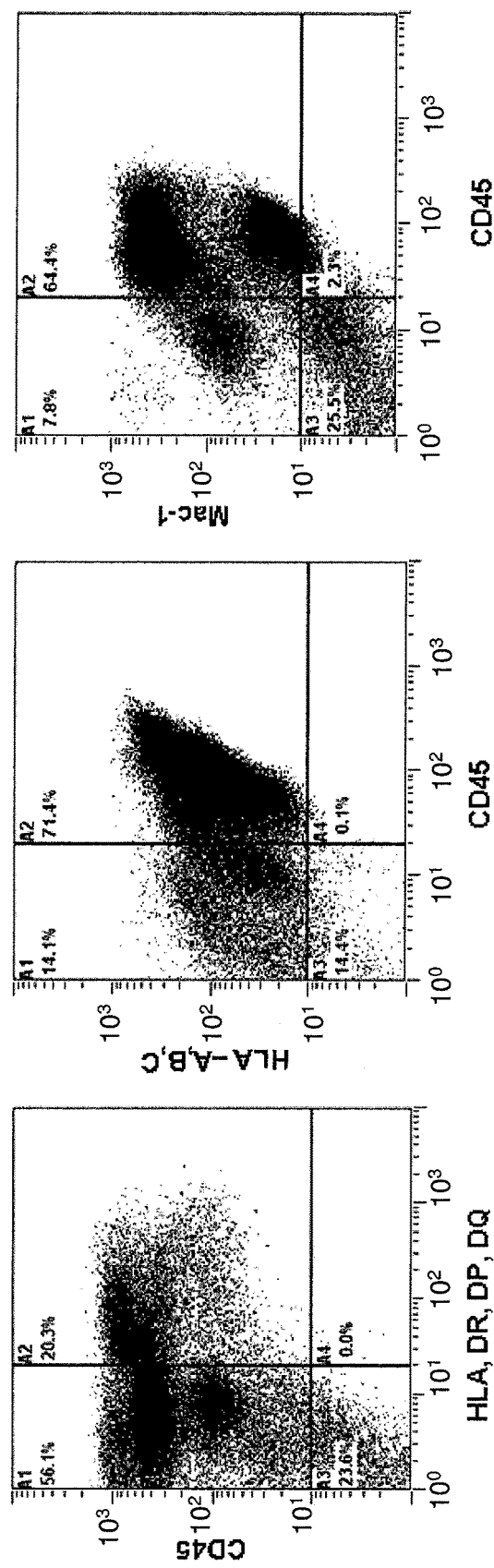
Figure 6B:
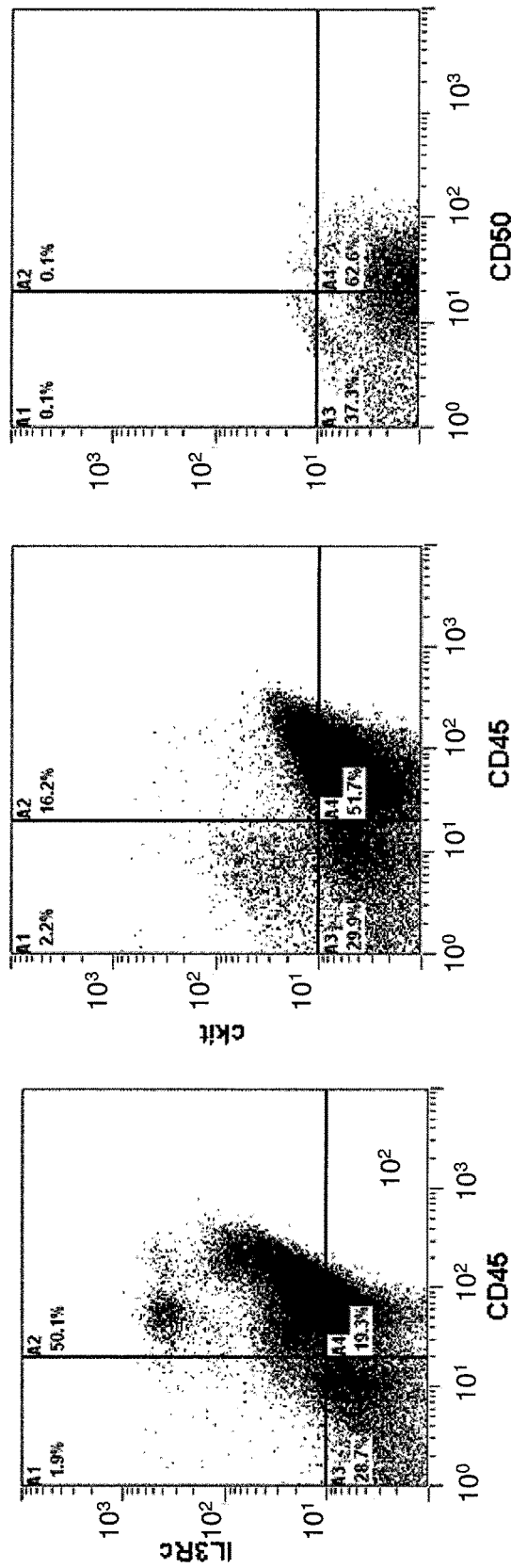
Figure 6B:
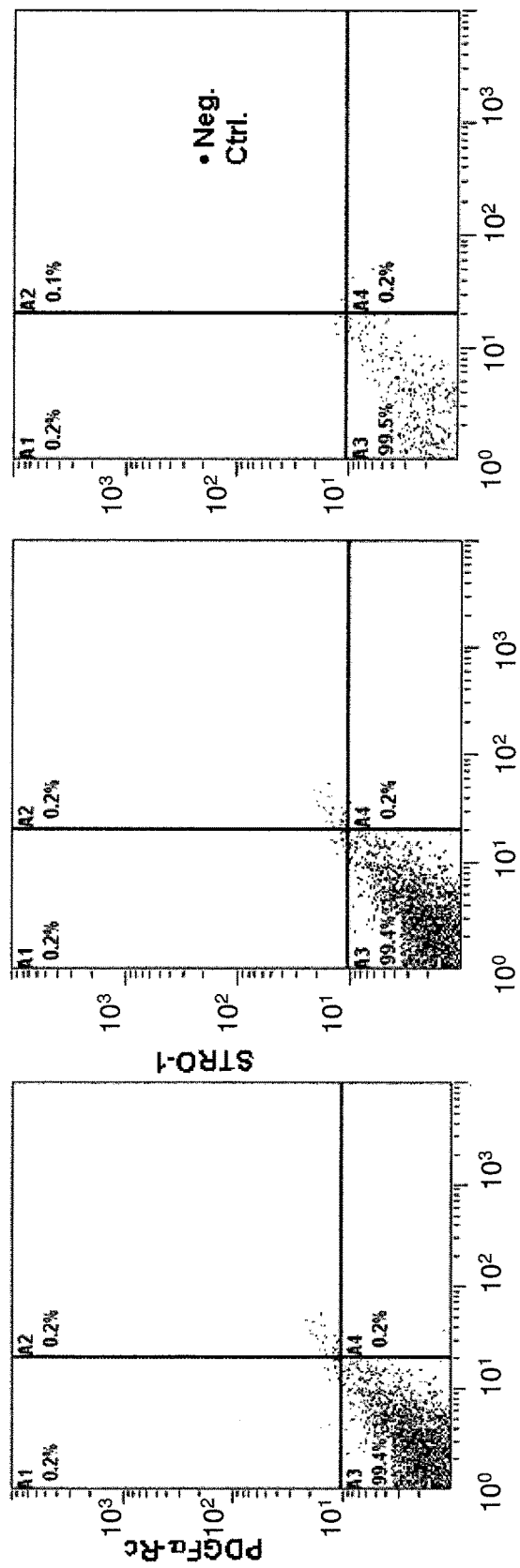
Figure 6C:
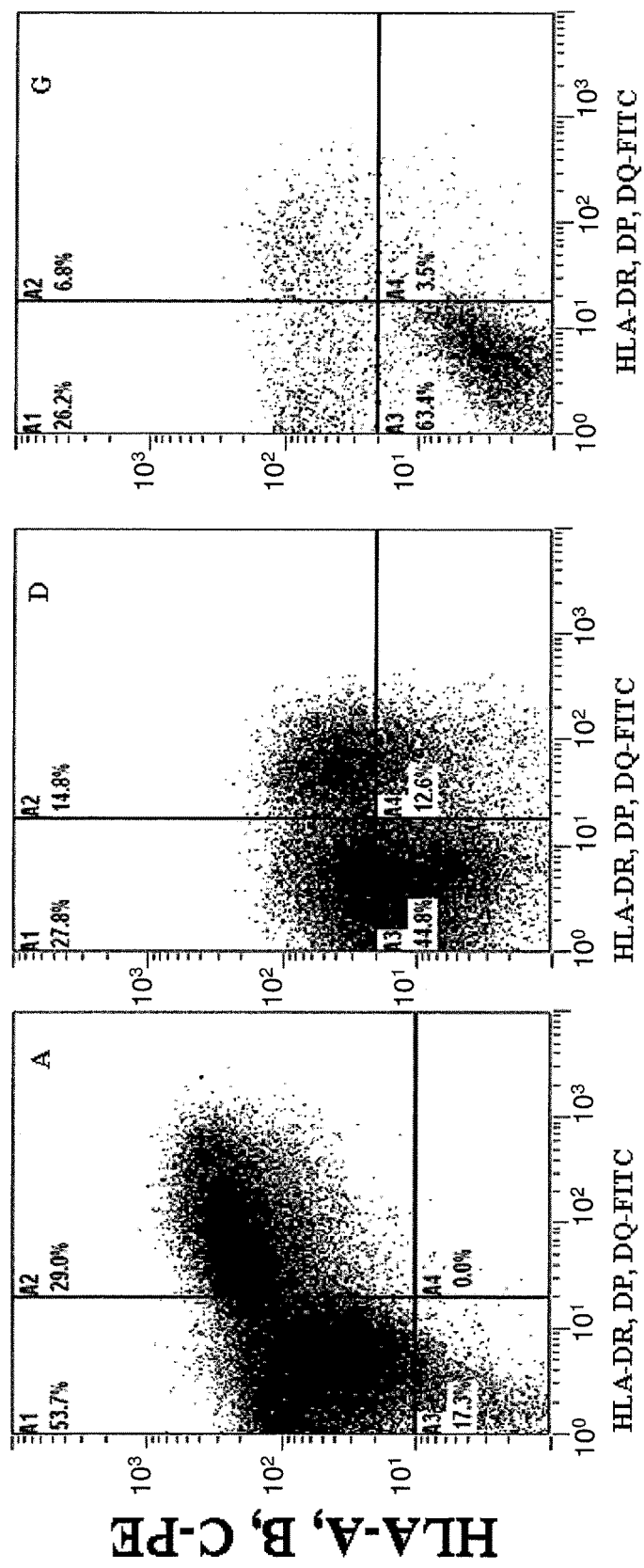
FIG. 6C shows flow cytometric analysis plots for expression of HLA-A, B, C and HLA-DP, DQ, DR markers, which correspond to MHC class I and MHC class II, respectively. Plotted is the expansion of the above discussed mark as on Ficolled Bone marrow cells (A, B and C), the population of cells grown in the presence of SCF+IL3 (D, E and F) and in the absence of cytokines (G) after 21 days of culture. Plot H is the negative control for the input population while plot I is the negative control for the SCF+IL3 and No Cytokines experiments.
Figure 6C:
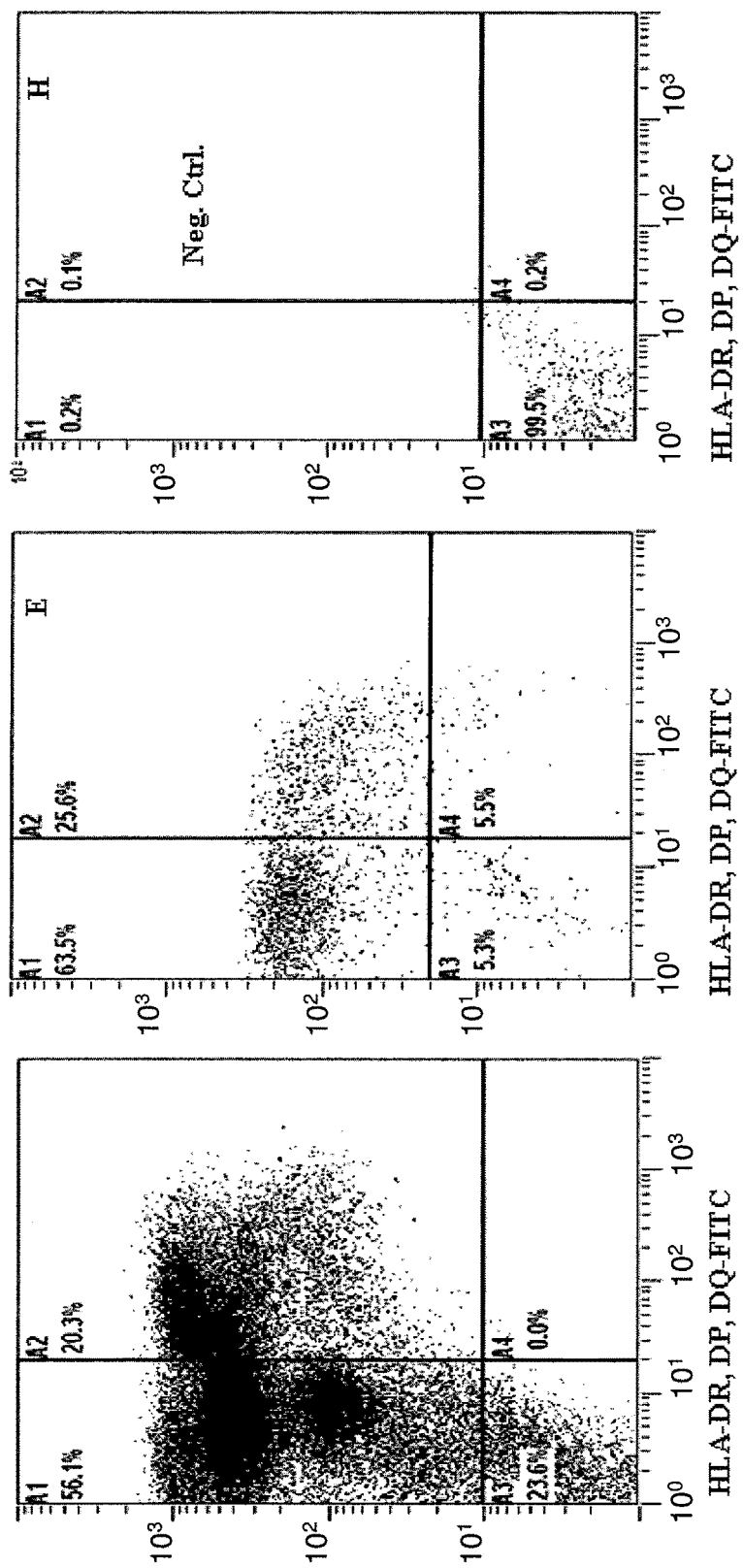

FIGS. 5A-D are SEM images taken of bone nodule cultures of Day 5 suspension cells that were grown in the various treatment groups studied. FIGS. 5A and 5B show cement line matrix covering the underlying substratum. This matrix is the initial matrix laid down by differentiating osteogenic cells (FIG. 5E). In FIGS. 5C and 5D shows mineralized collagen, comprising the nodular area. Transmission electron microscopy (FIG. 5F) confirmed that the matrix lining the culture dish comprises globular accretions that form the cement line matrix. After 3 weeks of suspension culture, bioreactor-derived cells maintained their capacity to form cement line matrix and mineralized collagen as seen in FIGS. 5G (No Cytokine condition) and 5H (SCF+IL3 condition).

Anti-collagen type I fluorescence stain was also performed on bioreactor-derived cells cultured in osteogenic conditions. Bone nodule cultures were initiated with cells derived from bioreactors supplemented with either no cytokines or SCF+IL3 and SCF+IL3+PDGF. After 5 weeks, bone nodule cultures were terminated and stained with primary anti-mouse collagen type 1 antibody followed by a secondary staining with Alex Fluor 488 goat anti-mouse antibody. The results confirmed, by vivid green staining in light micrographs, that cells removed from a bioreactor supplemented with SCF+IL3+PDGF (C, E), respectively, were producing collagen type I material.

Light micrographs of cells generated in the CFU-F assays of the PDGF-treated cultures suggested, based on morphology, that the cells maybe of neural origin. Consequently, cells grown in the presence of SCF+IL3+PDGF were initiated in CFU-F assays and at 2 weeks the cultures were washed in PBS and then fixed in 2.5% paraformaldehyde. The cells were permeabilized with 0.1% Triton-X 100 solution and then blocked with nonspecific goat serum (2% in PBS) prior to the addition of NeuN [mouse anti-NeuN monoclonal IgG$_1$ MoAb, 1:500 dilution, (Chemicon, Temecula, Calif.)]. The antibody was detected with a goat anti-mouse IgG MoAb conjugated with Alexa Fluor 594 (1:200 dilution, Molecular Probes, Eugene, Oreg.). To quantify the positive expressing NeuN cells, 10 random fields were imaged at 20× using an inverted microscope (Olympus CK40, Carson Group Inc., ON, Canada) and the average count was normalized to the surface area of the field area captured. Negative controls (cultures incubated with only secondary antibody) were run in parallel to confirm NeuN staining. NeuN appeared to localize to the nuclear area of the cell body as seen by the intense red staining in this region Day 7 bioreactor-derived cells from the No Cytokine, SCF+IL3 and SCF+IL3+PDGF were placed in medium supporting the growth and differentiation of myoblasts. The presence of an intercellular muscle protein, desmin, was used to identify colonies of myoblasts. Cultures were incubated with anti-mouse desmin monoclonal antibody followed by secondary staining with Alex Fluor 488 goat anti-mouse antibody. The results revealed an intense green staining throughout the cytoplasmic body of elongated cells lined closely together.

EXAMPLE 5

Phenotyping

Figure 7:
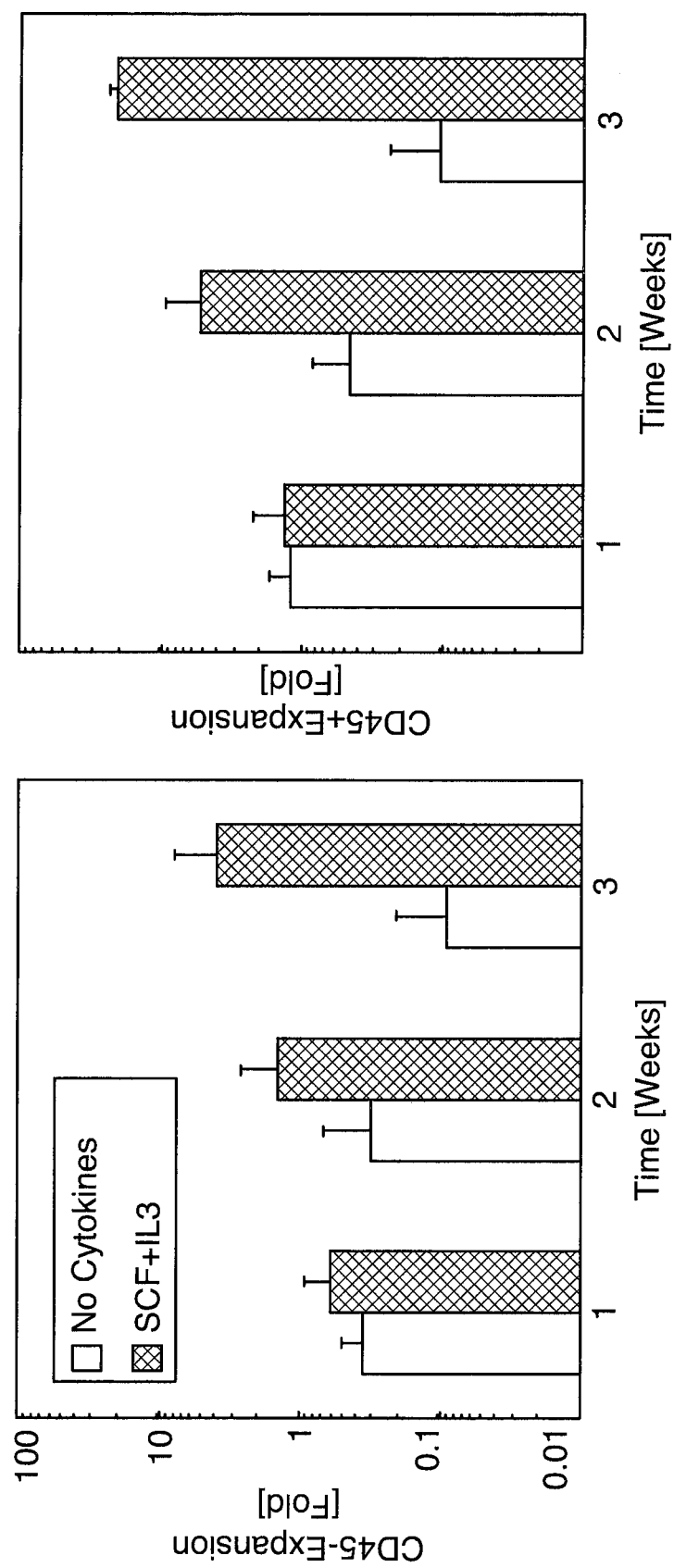
FIG. 7 reveals the calculated CD45⁻ and CD45⁺ cell expansion as determined by flow cytometric analysis of cells present in bioreactors at 1, 2 and 3 weeks. Greater CD45⁻ and CD45$^{low}$ cell expansion is achieved in the presence of SCF+IL3. Each bar represents the mean CD45⁻ and CD45⁺ cell number calculated from three independent flow cytometric analysis of bioreactor-derived cells at 1, 2 and 3 weeks.

FIGS. 6 and 7 illustrate the type and distribution, over the culture duration, of specific populations of cells generated from the input cell population. As noted, a shift in the distribution of the hematopoietic CD45 cells occurs over time, as a gradual reduction in cells of this type (FIG. 7). It will be noted that the progenitor population has a SH4 negative phenotype. The SH4 marker is alleged to be definitive of mesenchymal stem cells, suggesting that the present progenitor population is not homogeneous for this cell type.

Also as noted in FIG. 6, dot plots are provided for the HLA markers. Cells bearing these surface markers are involved in graft tissue rejection. The impact of suspension culturing on cells expressing these markers is elaborated in FIG. 6C. As is evident, the input population of FIG. 6B reveals a heterogeneous HLA cell population, which includes a "double negative" phenotype representing 17% of the population. Upon expansion culturing in the presence and absence of SCF+IL3 for 21 days, it is evident that there is an increase in the fraction of double negative cells (FIG. 6C, panels D and G). Moreover, from plots E and F, grown in the presence of SCF and IL3, it was determined that a fraction of the double negative population observed in plot D are CD45 expressing cells. In the absence of exogenously added cytokines, a larger fraction of double negative cells were present in the culture after 21 days of suspension culturing.

It will also be noted from FIG. 6 that cells expanded by suspension culturing include those expressing CD50, a marker associated with endothelial cells.

It will thus be appreciated that, in accordance with an embodiment of the present invention, non-static suspension culturing is a viable method for the expansion of progenitor cells that are of the HLA double negative phenotype. Such cells will be very useful in the engineering either ex vivo of in vivo of allogeneic tissues given that they have yet to commit to a lineage recognized as "self" by the recipient.

The results disclosed herein demonstrate that non-hematopoietic progenitor cells of the marrow parenchyma, including mesenchymal progenitor cells and particularly including osteoblast and adipocyte progenitor cells exist and remain viable in a long-term culture environment that is maintained in a stirred suspension bioreactor, as determined by their ability to form CFU-Fs and CFU-Os. Preliminary factorial design experiments involving the addition of cytokines and combination of cytokines that are potent mitogens for proliferation have demonstrated that cytokine addition can influence the output colony numbers as well the cells comprising the colony forming units. In addition, the cytokine supplementation appears to influence the potential of the cells maintained in suspension to form bone matrix in vitro when placed in an appropriate bone forming culture environment.

The progenitor cells maintained in suspension are multipotential, that is, they can form other differentiated phenotypes including bone, chondrocytes, adipocytes, endothelial cells, fibroblastic cells, neuron cells, bone marrow, myoblast cells and human cartilage. Once the human progenitor cells have been proliferated, some or all of the expanded cell population can be formulated with a suitable vehicle for delivery to a site at which differentiation into the desired cell or tissue type is desired. For instance, and as just described, the cells can be introduced into a tissue-forming environment scaled to be suitable either for assay or for growth of human tissues or cells on a small scale for transplantation. The input population to be cultured in the expansion bioprocess can be the input population of progenitor cells extracted from marrow parenchyma or a comparable source, or the input population can be an enriched, subpopulation thereof from which one or more hematopoietic cell phenotypes have been subtracted. It will be understood that the present invention is not restricted per se to humans and may be used for producing mesenchymal and other marrow parenchymal progenitor cells for non-human applications.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

Bruder S P, Jaiswal N, Haynesworth S E. Growth kinetics, self-renewal, and the osteogenic potential of purified human mesenchymal stem cells during extensive Subcultivation and following cyropreservation. J Cellular Biochemistry 1997;64:278-294.

Caplan AI, Bruder S P. Cell and molecular engineering of bone regeneration. In Principles of Tissue Engineering, edited by Lanza R, Langer T, Chick W. R. G. Landes Company, 1997, 603-617.

Castro-Malaspina H, Gay R E, Resnick G, Kappor N, Meyers P, Chiariere D, McKenzie S, Broxmeyer H E, Moore M A S. Characterization of human bone marrow fibroblast colony-forming cells (CFU-F) and their progeny. Blood 1980;56(2):289301.

Colter D C, Class R, DiGirolamo C M, Prockop D J. Rapid expansion of recycling stem cells in cultures of plastic-adherent cells from human bone marrow. PNAS 2000;97(7):3213-3218.

Davies J E, Chernecky R, Lowenberg B, Shiga A. Deposition and resorption of calcified matrix in vitro by rat marrow cells. Cells Mater 1991;1:3-15.

Davies J E. In vitro modeling of the bone/implant interface. Anat Rec 1996:245:426-445 Friedenstein, A J, Latzinkik N V, Gorskaya Y F, Lurie E A, Moskvina I L. Bone marrow stromal colony formation requires stimulation by hematopoietic cells. Bone and Mineral 1992; 18:199-213.

Gronthos S, Graves S E, Ohta S, Simmons P J. The STRO-1 fraction of adult human bone marrow contains the osteogenic precursors. Blood 1994;84(12):4164-4173.

Hu, W. Method of aggregating cells with small microspheres. U.S. Pat. No. 5,114,855, issued May 19, 1992.

Jacques, J. Method for the in vitro propagation and maintenance of cells (U.S. Pat. No.: 1973000376038), issued Dec. 14, 1976.

Jarvis, A P and Lim F. Method of culturing anchorage dependent cells. U.S. Pat. No. 4,495,288, issued Jan. 22, 1985.

Ohgushi H, Caplan A. Stem cell technology and bioceramics: From cell to gene engineering. J Biomed Mater Res (Appl Biomater) 1999;48:913-927.

Parker E, Shiga A and Davies J E. Growing human bone in vitro. Chapter 6 in: "Bone Engineering" [ed-J E Davies], EM squared In., Toronto, 2000.

Naughton, G K and Naughton B A. Three-dimensional cell and tissue culture system. U.S. Pat. No. 4,963,489, issued Oct. 16, 1990.

Simmons P J, Torok-Storb B. CD34 expression by stromal precursors in normal human adult bone marrow. Blood 1991;78(11):2848-2853.

Zandstra P W, Eaves C J, Piret J M. Expansion of hematopoietic progenitor cell population in stirred suspension bioreactors of normal human bone marrow cells. Bio/technology 1994;12:909-914.

Zandstra P W. Challenges Involved in the Development of Stem Cell-Based Technologies: Hematopoiesis, Osteogenesis and Beyond. Chapter 8 in: "Bone Engineering" [ed-J E Davies],EM squared Inc., Toronto, 2000.

We claim:

1. A method for expanding human bone marrow derived mesenchymal progenitor cells comprising the step of culturing said mesenchymal progenitor cells under non-static conditions such that said mesenchymal progenitor cells are expanded without adherence to the surface of the container in which the cells are cultured.

2. The method of claim 1 wherein said mesenchymal progenitor cells are expanded in a culture medium containing stem cell factor and interleukin-3.

3. The method of either of claim 1 or 2 wherein the mesenchymal progenitor cells are not adherence-selected prior to expansion.

* * * * *